(12) United States Patent
Nishiura et al.

(10) Patent No.: US 9,991,450 B2
(45) Date of Patent: Jun. 5, 2018

(54) SPIRO[CYCLOPENTA[DEF]TRI-PHENYLENE-4,9'-FLUORENE] COMPOUND AND ORGANIC LIGHT-EMITTING DEVICE HAVING THE SAME

(75) Inventors: Chiaki Nishiura, Kawasaki (JP); Jun Kamatani, Tokyo (JP); Naoki Yamada, Inagi (JP); Kenichi Ikari, Abiko (JP)

(73) Assignee: Canon Kabushiki Kaisha, Tokyo (JP)

( * ) Notice: Subject to any disclaimer, the term of this patent is extended or adjusted under 35 U.S.C. 154(b) by 304 days.

(21) Appl. No.: 13/881,359

(22) PCT Filed: Oct. 11, 2011

(86) PCT No.: PCT/JP2011/073772
§ 371 (c)(1),
(2), (4) Date: Apr. 24, 2013

(87) PCT Pub. No.: WO2012/056919
PCT Pub. Date: May 3, 2012

(65) Prior Publication Data
US 2013/0214267 A1    Aug. 22, 2013

(30) Foreign Application Priority Data

Oct. 27, 2010    (JP) .................................. 2010-241203
Jul. 20, 2011    (JP) .................................. 2011-159077

(51) Int. Cl.
*H01L 51/50* (2006.01)
*H01L 51/00* (2006.01)
(Continued)

(52) U.S. Cl.
CPC .......... *H01L 51/0074* (2013.01); *C07C 13/72* (2013.01); *C07C 49/792* (2013.01);
(Continued)

(58) Field of Classification Search
CPC . H05B 33/10; H01L 51/0074; H01L 51/0054; H01L 51/0058; H01L 51/0061;
(Continued)

(56) References Cited

U.S. PATENT DOCUMENTS 5,026,894 A    6/1991    Tour
5,840,217 A    11/1998    Lupo
(Continued)

FOREIGN PATENT DOCUMENTS

JP    2000-150164 A    5/2000
JP    2007-332139 A    12/2007

OTHER PUBLICATIONS

Montalti et al., Handbook of Photochemistry, Third Edition, 2006, pp. 195-202) (Year: 2006)*
(Continued)

*Primary Examiner* — Jennifer A Chriss
*Assistant Examiner* — Dylan C Kershner
(74) *Attorney, Agent, or Firm* — Canon U.S.A., Inc. IP Division

(57) ABSTRACT

A spiro[cyclopenta[def]triphenylene-4,9'-fluorene] compound having a high triplet energy level and a high glass transition temperature further providing an excellent organic light-emitting device including the compound to achieve a high luminous efficiency and a low driving voltage.

19 Claims, 1 Drawing Sheet

(51) Int. Cl.

| | | |
|---|---|---|
| *C07C 13/72* | (2006.01) | |
| *C07C 49/792* | (2006.01) | |
| *C07C 211/61* | (2006.01) | |
| *C07D 333/76* | (2006.01) | |
| *C09K 11/06* | (2006.01) | |
| *H05B 33/10* | (2006.01) | |

(52) U.S. Cl.
CPC .......... *C07C 211/61* (2013.01); *C07D 333/76* (2013.01); *C09K 11/06* (2013.01); *H01L 51/0054* (2013.01); *H01L 51/0058* (2013.01); *H01L 51/0061* (2013.01); *H01L 51/0062* (2013.01); *H01L 51/5072* (2013.01); *H05B 33/10* (2013.01); *C07C 2603/18* (2017.05); *C07C 2603/94* (2017.05); *C09K 2211/1007* (2013.01); *C09K 2211/1011* (2013.01); *C09K 2211/1014* (2013.01); *C09K 2211/1092* (2013.01); *H01L 51/006* (2013.01); *H01L 51/0072* (2013.01); *H01L 51/0085* (2013.01); *H01L 51/5016* (2013.01); *H01L 51/5056* (2013.01); *H01L 51/5096* (2013.01)

(58) Field of Classification Search
CPC ............. H01L 51/0062; H01L 51/5072; H01L 51/006; H01L 51/0072; H01L 51/0085; H01L 51/5016; H01L 51/5056; H01L 51/5096; H01L 51/0051; H01L 51/0052; H01L 51/50; H01L 51/5012; C09K 2211/1007; C09K 2211/1011; C09K 2211/1014; C09K 2211/1092; C09K 11/06; C07C 2103/94; C07C 2103/18; C07C 333/76; C07C 211/61; C07C 49/792; C07C 13/72
USPC .................... 428/690, 691, 917; 427/58, 66; 313/500–512; 257/40, 88–104, 257/E51.001–E51.052; 252/301.16–301.35; 549/43; 564/427; 568/326; 585/27
See application file for complete search history.

(56) References Cited

U.S. PATENT DOCUMENTS

| | | | |
|---|---|---|---|
| 6,416,887 B1* | 7/2002 | Tokito | C07C 211/61 313/504 |
| 2002/0034659 A1* | 3/2002 | Nishi | H01L 51/0094 428/690 |
| 2002/0182441 A1* | 12/2002 | Lamansky | C07F 15/0033 428/690 |
| 2004/0076853 A1* | 4/2004 | Jarikov | 428/690 |
| 2005/0158583 A1* | 7/2005 | Kim | C08G 61/00 428/690 |
| 2006/0088728 A1* | 4/2006 | Kwong | C07D 209/82 428/690 |
| 2006/0113898 A1* | 6/2006 | Toyoda | B41J 2/45 313/504 |
| 2006/0227081 A1* | 10/2006 | Joo et al. | 345/76 |
| 2006/0280965 A1* | 12/2006 | Kwong | C07C 13/62 428/690 |
| 2007/0290610 A1* | 12/2007 | Park | C07C 211/54 313/504 |
| 2009/0045730 A1* | 2/2009 | Nishimura | C09K 11/06 313/504 |
| 2009/0092853 A1 | 4/2009 | Park | |
| 2013/0175519 A1* | 7/2013 | Yamada et al. | 257/40 |

OTHER PUBLICATIONS

Suhee Song et al., A novel conjugated polymer based on cyclopenta [def] phenanthrene backbone with spiro group, Polymer 49 2008. 10.012, 5643-5649.

Steven L. Murov, et al., Handbook of Photochemistry, Second Edition, Revised and Expanded, Marcel Dekker, Inc., New York; pp. 102-127.

* cited by examiner

FLUORENE GROUP

TRIPHENYLENE GROUP

SPIRO[CYCLOPENTA[DEF]TRI-PHENYLENE-4,9'-FLUORENE] COMPOUND AND ORGANIC LIGHT-EMITTING DEVICE HAVING THE SAME

TECHNICAL FIELD

The present invention relates to spiro[cyclopenta[def]triphenylene-4,9'-fluorene] compounds and organic light-emitting devices having the same.

BACKGROUND ART

An organic light-emitting device includes an anode, a cathode, and an organic compound layer disposed between the electrodes. In the organic light-emitting device, holes and electrons that are injected to the organic compound layer from the anode and the cathode, respectively, are recombined to generate excitons, and light is emitted when the excitons return to the ground state. The organic light-emitting device has remarkably progressed recently, and it is possible to provide light-emitting devices that are driven with low voltages, emit various emission wavelengths, and are rapidly responsive, thin, and lightweight.

A phosphorescent device is an organic light-emitting device that includes a phosphorescent material in the organic compound layer and emits light due to the triplet excitons, and there is a demand for further improvement in luminous efficiency of the phosphorescent device.

As the material for the light-emitting layer of the organic light-emitting device, for example, PTL 1 describes Compound H01, PTL 2 describes Compound H02, and PTL 3 describes Compound H03. These compounds are shown below. Note that the terms H01 to H03 are names given in this description.

[Chem. 1]

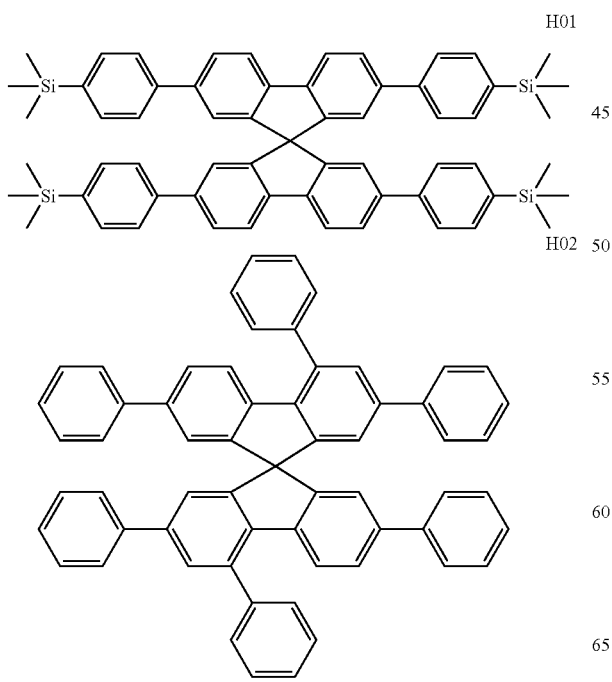

H01

H02

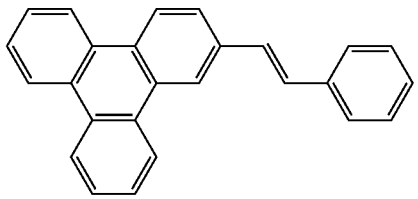

H03

CITATION LIST

Patent Literature

PTL 1 U.S. Pat. No. 5,026,894
PTL 2 U.S. Pat. No. 5,840,217
PTL 3 Japanese Patent Laid-Open No. 2000-150164

SUMMARY OF INVENTION

The compounds disclosed in PTLs 1 and 2 have 9,9'-spirobi[fluorene] as the basic skeletons, and, therefore, the difference between the triplet energy (T1 energy) level and the singlet energy (S1 energy) level is large. Accordingly, the driving voltages of phosphorescent devices produced using these compounds as raw materials are high. Meanwhile, the compound disclosed in PTL 3 includes a triphenylene group having high planarity and thereby shows high crystallinity, resulting in low film-forming property.

The present invention provides a spiro[cyclopenta[def]triphenylene-4,9'-fluorene] compound that has a small difference between the T1 and S1 energy levels and a high film-forming property. The present invention further provides an organic light-emitting device that includes the compound and has a high luminous efficiency and a low driving voltage.

The present invention provides spiro[cyclopenta[def]triphenylene-4,9'-fluorene] compounds represented by the following General Formula [1]:

[Chem. 2]

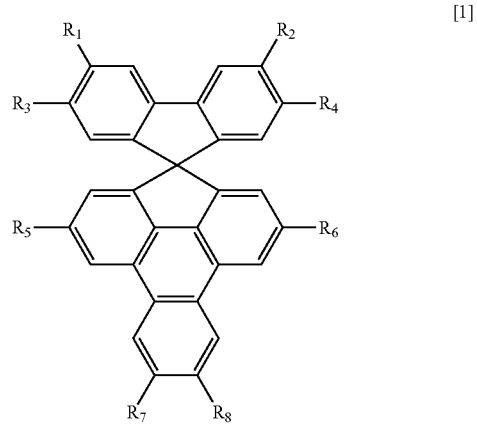

[1]

In General Formula [1], $R_1$ to $R_8$ are independently selected from the group consisting of hydrogen atoms, phenyl groups, biphenyl groups, terphenyl groups, naphthyl groups, phenanthryl groups, triphenylene groups, fluorenyl groups, dibenzothiophene groups, carbonyl groups, amino groups, and spiro[cyclopenta[def]triphenylene-4,9'-fluorene] groups.

The phenyl groups, the biphenyl groups, the terphenyl groups, the naphthyl groups, the phenanthryl groups, the triphenylene groups, the fluorenyl groups, the dibenzothiophene groups, the carbonyl groups, the amino groups, and the spiro[cyclopenta[def]triphenylene-4,9'-fluorene] groups may optionally have substituents selected from alkyl groups, phenyl groups, carbonyl groups having phenyl groups, substituted amino groups, and dibenzothiophene groups.

According to the present invention, new compounds having small differences between the triplet and singlet energy levels and high glass transition temperatures can be provided. In addition, organic light-emitting devices having high luminous efficiencies and low driving voltages can be provided by using the compounds.

DESCRIPTION OF EMBODIMENTS

Figure 1:
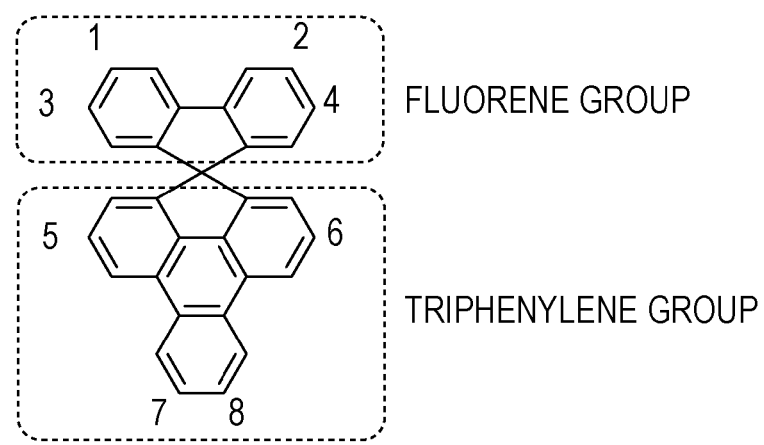
FIG. 1 is a schematic diagram illustrating substitution positions of compounds according to the present invention.

Spiro[cyclopenta[def]triphenylene-4,9'-fluorene] compounds according to the present invention will be described. Hereinafter, the spiro[cyclopenta[def]triphenylene-4,9'-fluorene] compounds may be also referred to as compounds according to the present invention.

The present invention relates to spiro[cyclopenta[def]triphenylene-4,9'-fluorene] compounds represented by the following General Formula [1]:

[Chem. 3]

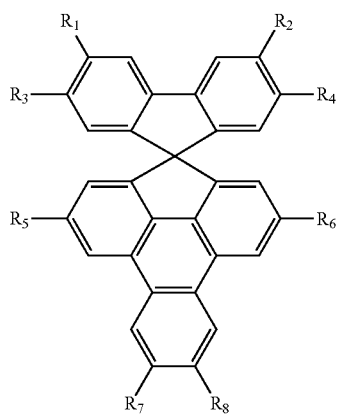

[1]

In General Formula [1], $R_1$ to $R_8$ are independently selected from the group consisting of hydrogen atoms, phenyl groups, biphenyl groups, terphenyl groups, naphthyl groups, phenanthryl groups, triphenylene groups, fluorenyl groups, dibenzothiophene groups, carbonyl groups, amino groups, and spiro[cyclopenta[def]triphenylene-4,9'-fluorene] groups.

The above-mentioned substituents may further have substituents. Examples of the optional substituents include alkyl groups such as a methyl group, an ethyl group, and a butyl group; hydrocarbon aromatic ring groups such as a phenyl group, a naphthyl group, a phenanthryl group, and a 9,9-dimethylfluorenyl group; heteroaromatic ring groups such as a thienyl group, a pyrrolyl group, a pyridyl group, and a dibenzothiophene group; substituted amino groups such as a dimethylamino group, a diethylamino group, a dibenzylamino group, a diphenylamino group, a ditolylamino group, and a dianisolylamino group; carbonyl groups having phenyl groups; alkoxy groups such as a methoxy group and an ethoxy group; aryloxy groups such as a phenoxy group and a naphthoxy group; halogen atoms such as fluorine, chlorine, bromine, and iodine; and hydroxyl groups, cyano groups, nitro groups, and spiro[cyclopenta[def]triphenylene-4,9'-fluorene] groups.

Among the above-mentioned substituents, in particular, an alkyl group having 1 to 4 carbon atoms, a substituted amino group, a dibenzothiophene group, a carbonyl group having a phenyl group, or a spiro[cyclopenta[def]triphenylene-4,9'-fluorene] group can be used.

Properties of Compounds According to the Present Invention

The basic skeleton of compounds according to the present invention has a small difference between the singlet energy (S1 energy) level and the triplet energy (T1 energy) level and a high glass transition temperature. In this description, the basic skeleton is that shown as skeleton of the invention in the following Table 1.

Table 1 shows S1 energy, T1 energy, differences between the S1 and T1 energy levels, and glass transition temperatures of the basic skeleton of compounds according to the present invention, triphenylene, 9,9'-spirobi[fluorene], and fluorene.

TABLE 1

|   | Structural formula | Singlet energy | Triplet energy | Energy difference between singlet and triplet states | Glass transition temperature |
|---|---|---|---|---|---|
| Skeleton of the invention |   | 3.52 eV | 2.88 eV | 0.64 eV | 120° C. |

TABLE 1-continued

| | Structural formula | Singlet energy | Triplet energy | Energy difference between singlet and triplet states | Glass transition temperature |
|---|---|---|---|---|---|
| 9,9'-Spirobi[fluorene] | | 3.94 eV | 2.86 eV | 1.08 eV | Not detected |
| Triphenylene | | 3.52 eV | 2.88 eV | 0.64 eV | Not detected |
| Fluorene | | 4.12 eV | 2.92 eV | 1.19 eV | Not detected |

It is confirmed from Table 1 that the difference between the S1 and T1 energy levels of the basic skeleton of compounds according to the present invention is smaller than those of 9,9'-spirofluorene and fluorene.

Basically, the materials used for organic light-emitting devices can be compounds having small S1 energy levels. This is because the driving voltage is low when the S1 energy of the material is low.

Meanwhile, phosphorescent devices emit light using the T1 energy. In phosphorescence, the T1 energy level necessary for phosphorescence depends on the emission color.

That is, in the phosphorescent device, the S1 energy is required to be lowered while a necessary T1 energy level being maintained, i.e., a small difference between the S1 and T1 energy levels is required.

The basic skeleton of compounds according to the present invention and triphenylene have high T1 energy levels and small differences between the S1 and T1 energy levels and can be therefore used as materials of phosphorescent devices.

The basic skeleton of compounds according to the present invention has a glass transition temperature of 120° C. This temperature is higher than that of triphenylene. Accordingly, the compounds having this basic skeleton can be expected to have high film-forming properties, compared to triphenylene compounds.

In this description, the term "high film-forming property" means that an amorphous state can be maintained without causing crystallization even at high temperature. An example of measured value for the film-forming property is a glass transition temperature. A compound having a high glass transition temperature has a high film-forming property. A low film-forming property may have high crystallinity.

Meanwhile, glass transition temperatures could not be detected in triphenylene, 9,9'-spirobi[fluorene], and fluorene. This is because the glass transition temperatures of these compounds are too low to be detected. Note that Chem. Eur. J, 2007, 13, 10055-10069 describes that glass transition temperature of 9,9'-spirobi[fluorene] could not be detected.

In addition, it is known that triphenylene has high planarity and is thereby high in crystallinity and that the glass transition temperature cannot be detected.

The basic skeleton of compounds according to the present invention has a spiro structure that exhibits high steric hindrance against triphenylene, which suppresses planarity to show low crystallinity. That is, the film-forming property is high.

In addition, since the π-conjugated system is disconnected at the quaternary carbon of the spiro center, the molecular weight can be increased without changing the S1 and T1 energy levels. A larger molecular weight can reduce crystallinity.

The basic skeleton of compounds according to the present invention can simultaneously solve both a problem of high crystallinity of triphenylene and a problem of large difference between the S1 and T1 energy levels of 9,9'-spirobi [fluorene].

One characteristic of the basic skeleton of compounds according to the present invention is a high triplet energy level. In the phosphorescence spectrum of a diluted solution of the basic skeleton according to the present invention in toluene at 77 K, the triplet energy is obtained at 431 nm, which is a level higher than the blue region (440 to 480 nm).

Next, the substitution positions in compounds according to the present invention will be described with reference to FIG. 1. In the cases of compounds having substituents at substitution positions not being numbered in FIG. 1, the synthesis yield of the spiro[cyclopenta[def]triphenylene-4, 9'-fluorene] skeleton is significantly low due to steric hindrance. Accordingly, it is undesirable to have substituents at the positions not being numbered.

The numbers shown in FIG. 1 differ from substitution positions according to, for example, IUPAC.

In order to estimate the T1 energy level of a compound according to the present invention, the T1 energy levels of substituents that bind to $R_1$ to $R_8$ in General Formula [1] are paid attention to. Table 2 shows T1 energy levels (wavelength equivalents) of aryl groups and condensed polycyclic groups. These substituents have T1 energy levels higher than the blue region (440 to 480 nm) and can be applied to a region from blue to red (440 to 620 nm) in a combination thereof.

TABLE 2

| Substituent name | Structural formula | Triplet energy |
|---|---|---|
| Phenyl | | 339 |
| Biphenyl | | 436 |
| Terphenyl | | 445 |
| Naphthalene | | 469 |
| Phenanthrene | | 465 |
| Fluorene | | 424 |
| Triphenylene | | 430 |
| Dibenzothiophene | | 420 |

TABLE 2-continued

| Substituent name | Structural formula | Triplet energy |
|---|---|---|
| Skeleton of the invention | | 431 |
| Phenyl | | 339 nm |
| Biphenyl | | 436 nm |
| Terphenyl | | 445 nm |
| Naphthalene | | 469 nm |
| Phenanthrene | | 465 nm |
| Fluorene | | 424 nm |
| Triphenylene | | 430 nm |
| Dibenzothiophene | | 420 nm |

TABLE 2-continued

| Substituent name | Structural formula | Triplet energy |
| --- | --- | --- |
| Skeleton of the invention | | 431 nm |

In order to keep the S1 and T1 energy levels high, a substituent can be located at a position to which π-conjugated system is hardly connected, that is, at least either the position 1 or 2 in FIG. 1.

A high film-forming property can be achieved, without reducing the S1 and T1 energy levels, by introducing a substituent into the substitution position 1 or 2.

In order to reduce the S1 and T1 energy levels, a substituent having π-conjugation, such as an aryl group, can be located at a position to which π-conjugated system is connected, that is, the position 3 or 4 of the fluorene group or the position 5 or 6 of the triphenylene group in FIG. 1.

In the phosphorescent device having a phosphorescent material as the light-emitting material, the T1 energy level can be high.

Furthermore, a single molecule can have two different functions by appropriately introducing a substituent or substituents into the positions 1 to 8 in FIG. 1.

For example, by introducing a carbonyl group, which is excellent in electron-transporting property, into at least one of the substitution positions 1 to 4 in FIG. 1, functional separation such that electron transportation is performed on the fluorene side while hole transportation is performed on the triphenylene side is possible.

This is caused by that the π-conjugated system is disconnected at the spiro moiety. Moieties of which conjugated systems are disconnected hardly affect each other.

If a substituent such as an aryl group is located at the substitution position 3 or 4, the T1 energy is reduced. Accordingly, in order to keep the T1 energy level high, the substituent can be introduced into the substitution position 1 or 2. Both the substitution positions 1 and 2 may have substituents.

In addition, in light of the method of synthesizing compounds according to the present invention, compounds having substituents at the position 7 or 8 can be synthesized more easily than compounds having substituents at 5 or 6.

A substituent introduced into any of the substitution positions 5 to 8 can add steric hindrance of the substituent itself to the triphenylene group, in addition to the steric hindrance of the spiro structure.

The compounds according to the present invention can have reduced crystallinity compared to triphenylene and thereby have high film-forming properties.

The compounds according to the present invention can be used as the host materials of the electron-transporting layers, the hole-transporting layers, or the light-emitting layers of phosphorescent devices in a broad emission color range. In particular, the compounds can be used as the host materials of light-emitting layers.

Throughout the description, the host material of a light-emitting layer is a compound of which weight ratio is the highest in the compounds constituting the light-emitting layer. The guest material is a compound of which weight ratio is less than that of the host material in the compounds constituting the light-emitting layer and is a main material for the light emission. The assist material is a compound of which weight ratio is less than that of the host material in the compounds constituting the light-emitting layer and assists the light emission of the guest material.

The compound according to the present invention that is used as the host material of the electron-transporting layer, the hole-transporting layer, or the light-emitting layer of an organic light-emitting device can have appropriate S1 and T1 energy levels in light of emission color of the light-emitting material.

Furthermore, the compound according to the present invention can change HOMO-LUMO levels by appropriately selecting the substituent. For example, deep HOMO-LUMO levels can be obtained by introducing a carbonyl group. By using such a compound as the host material of an electron-transporting layer, a hole-blocking layer, or a light-emitting layer, the driving voltage of the device can be reduced.

This is because a deep LUMO level reduces the barrier for electron injection from the electron-transporting layer or the hole-blocking layer adjoining the light-emitting layer on the cathode side.

As described above, the compounds according to the present invention have high film-forming properties and high T1 energy levels.

Examples of the specific structural formulae of compounds according to the present invention are shown below.

[Chem. 4]
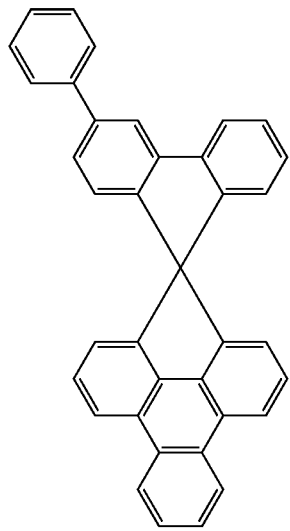
A01
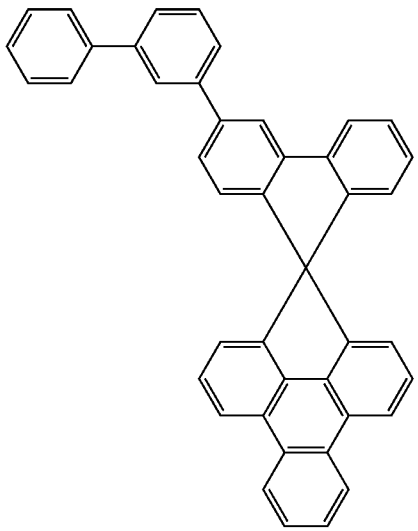
A02
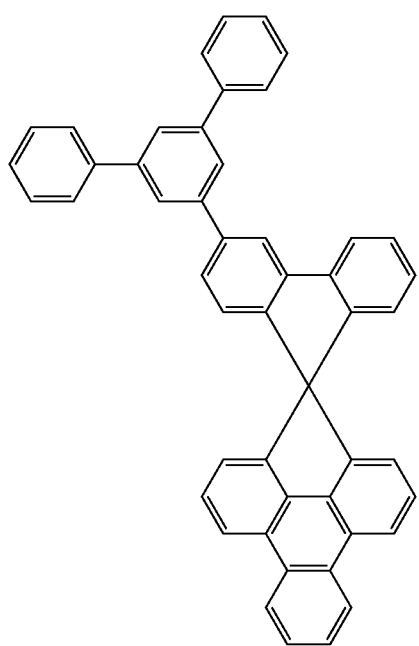
A03
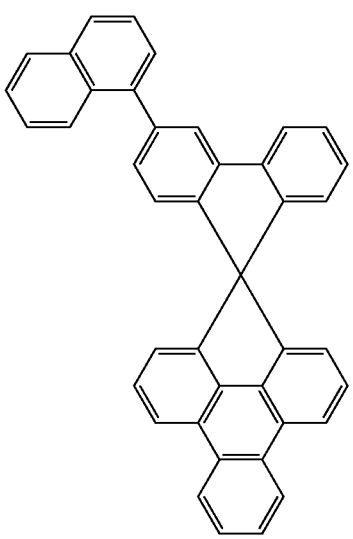
A04

-continued
A05
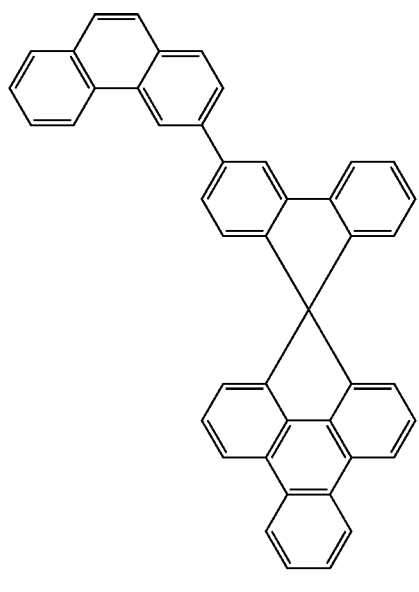
A06
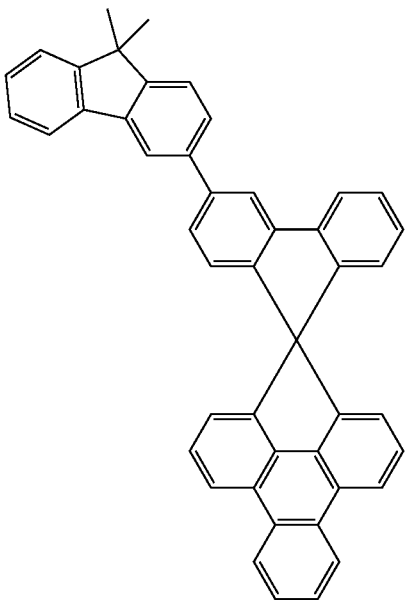
A07
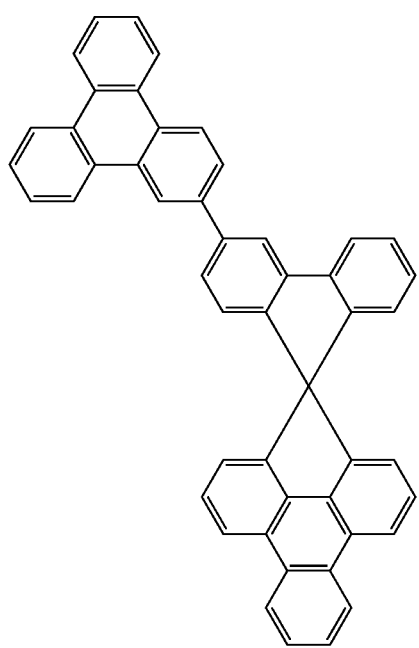
A08
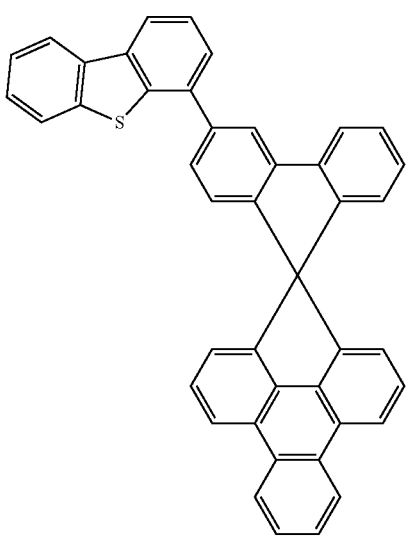

-continued
| | |
|---|---|
| A09 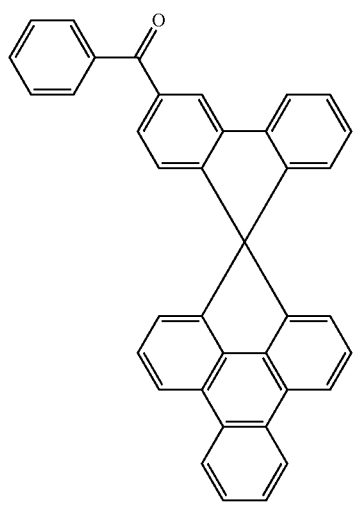 | A10 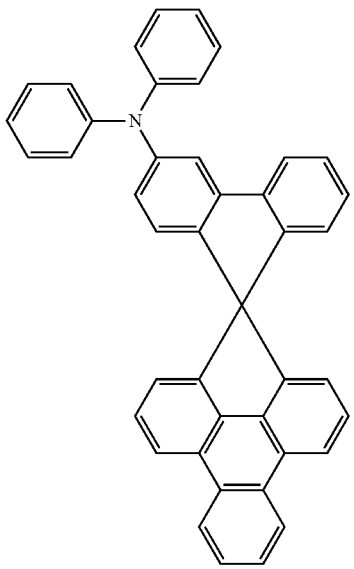 |
| 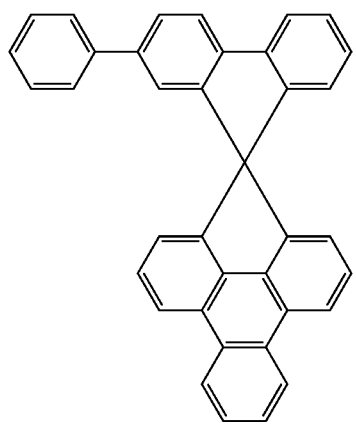 | A11 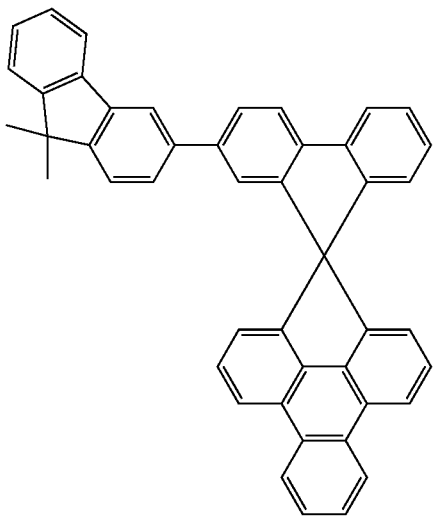 A12 |
| 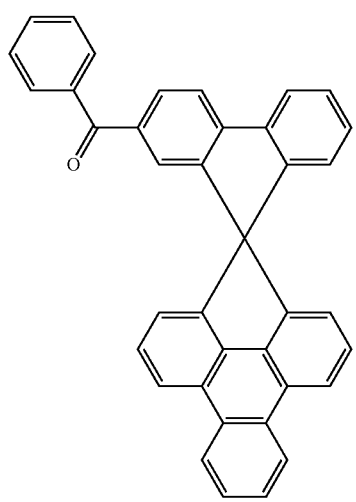 | A13 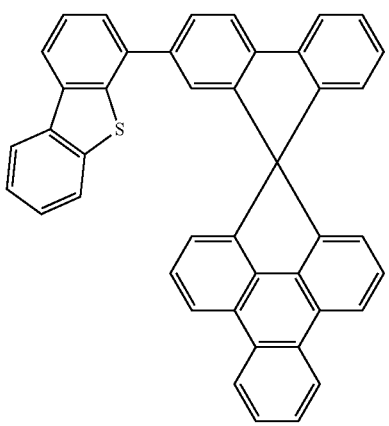 A14 |

-continued
A15
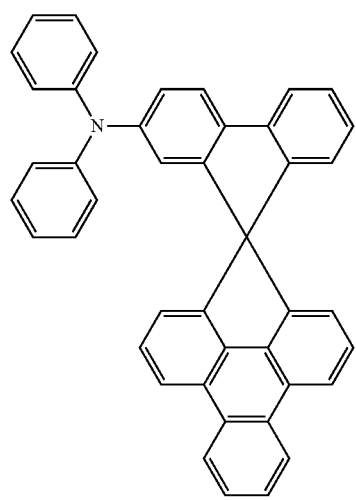
A16
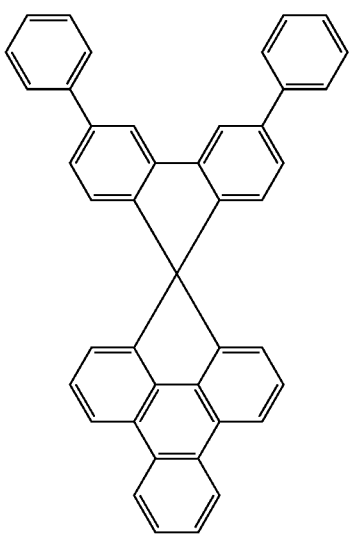
A17
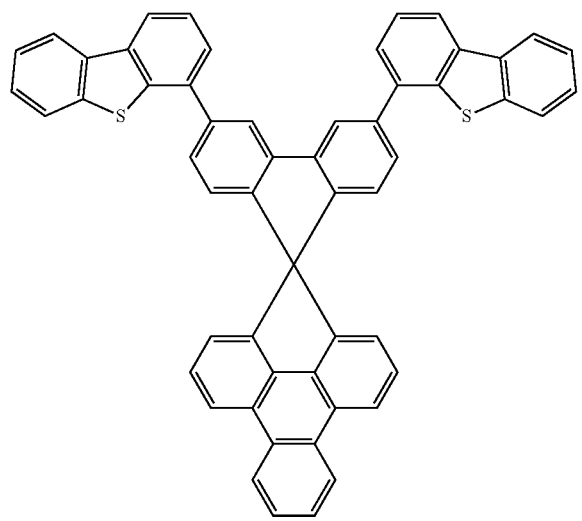
A18
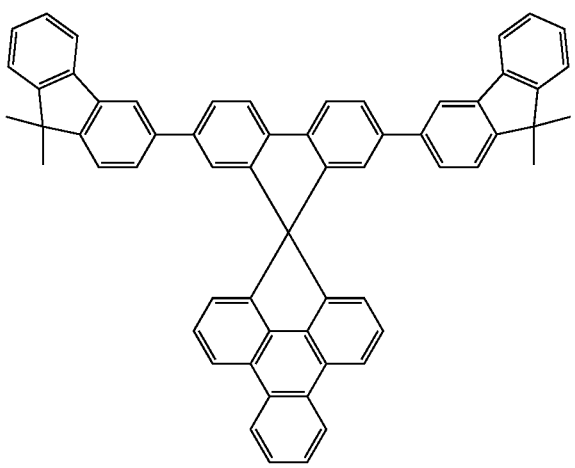
A19
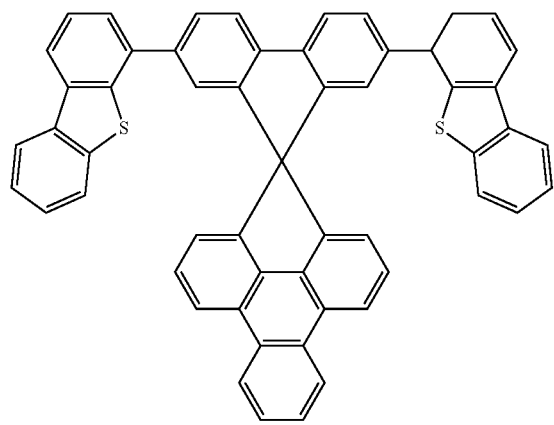
A20
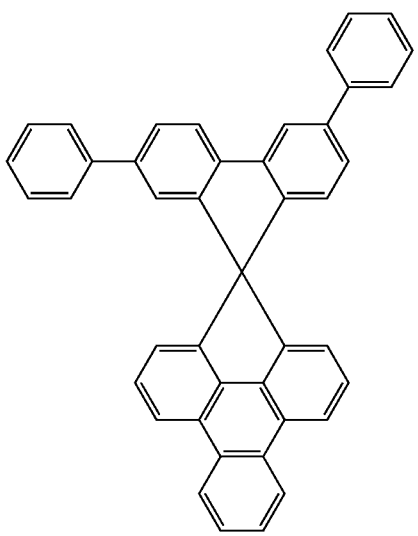

-continued
A21
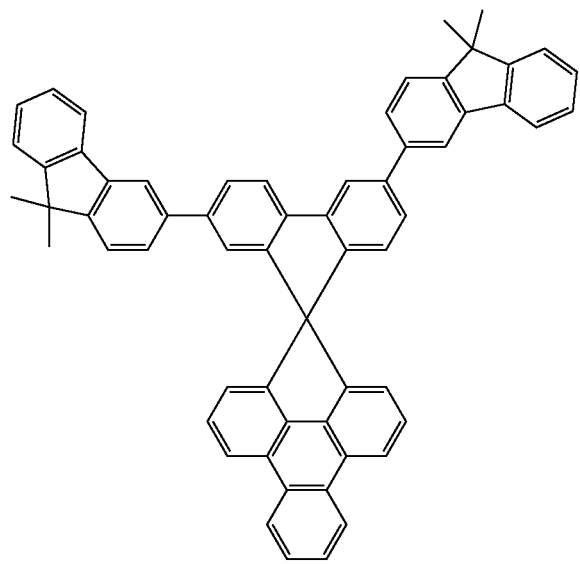
A22
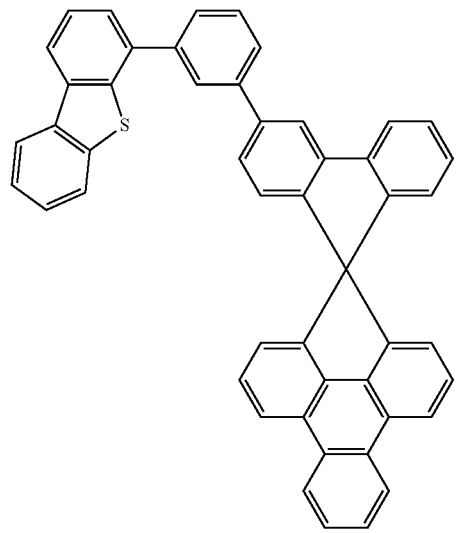
A23
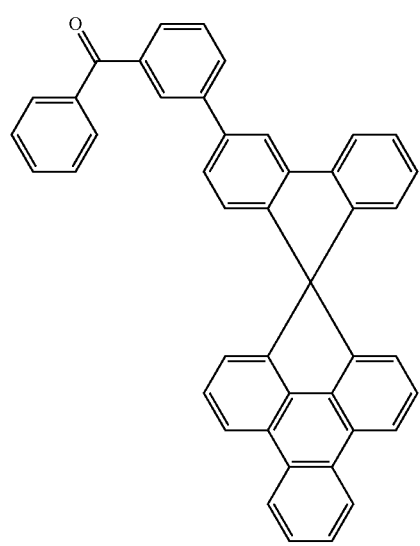
A24
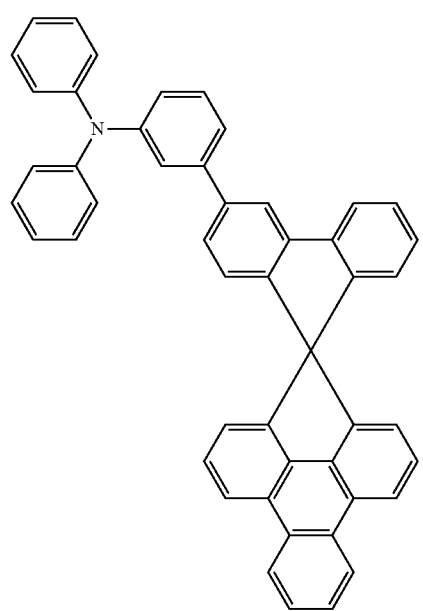

-continued
[Chem. 5]
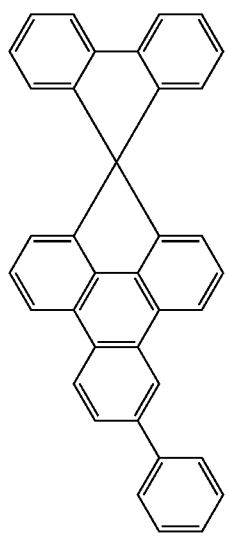
B01
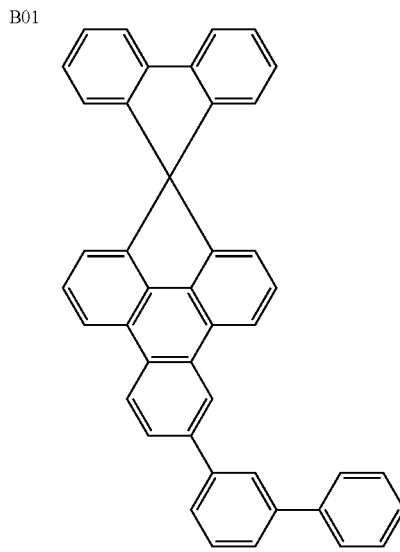
B02
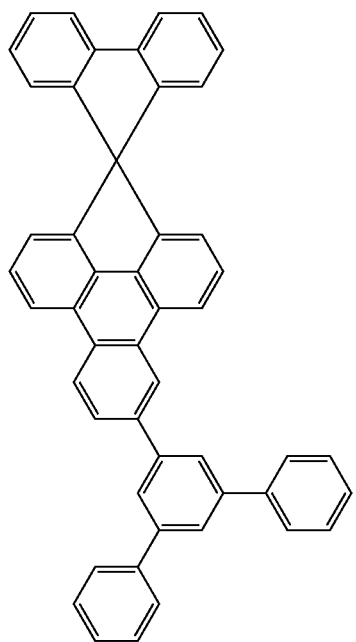
B03
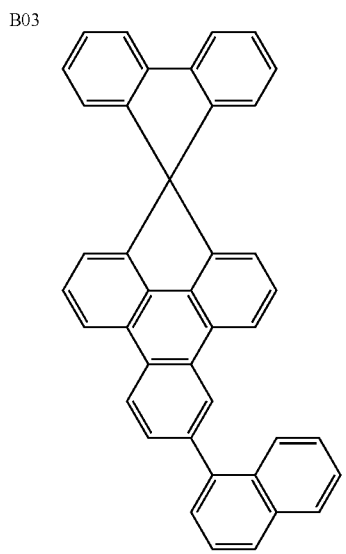
B04

-continued
B05
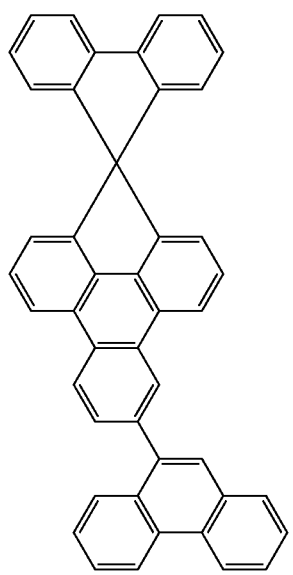
B06
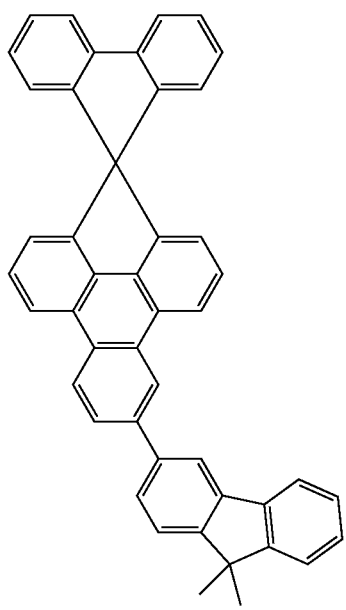
B07
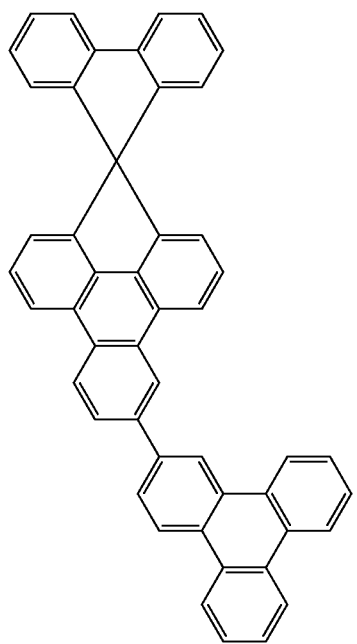
B08
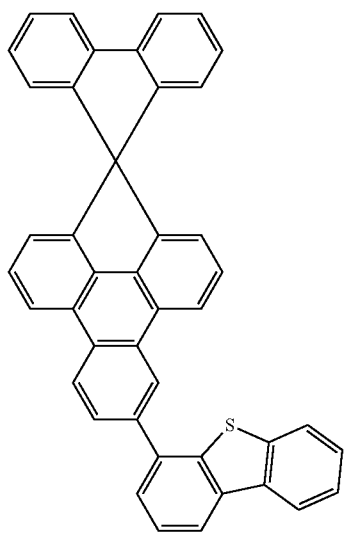

-continued
B09
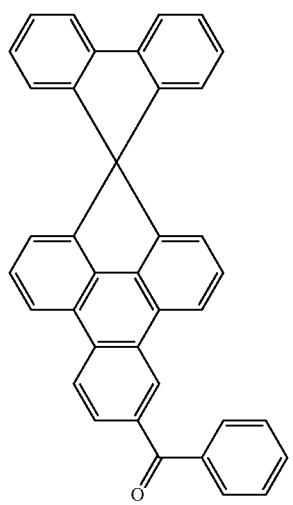
B10
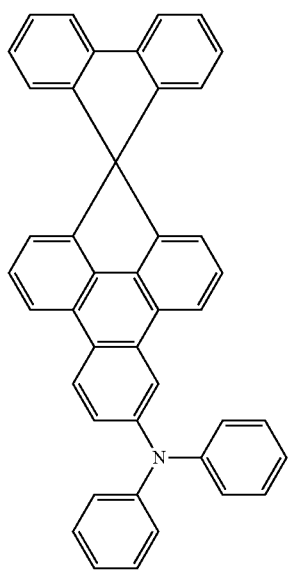
B11
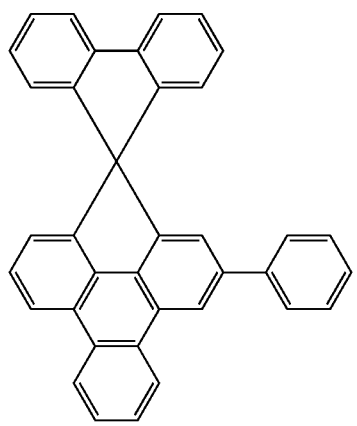
B12
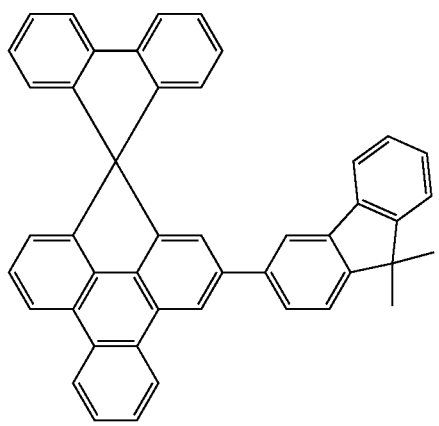
B13
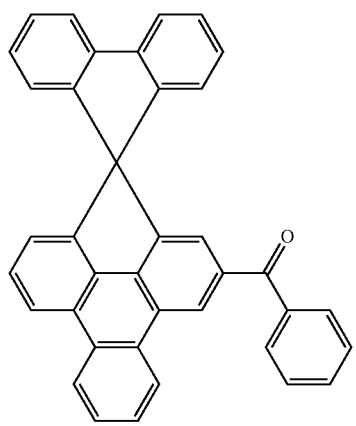
B14
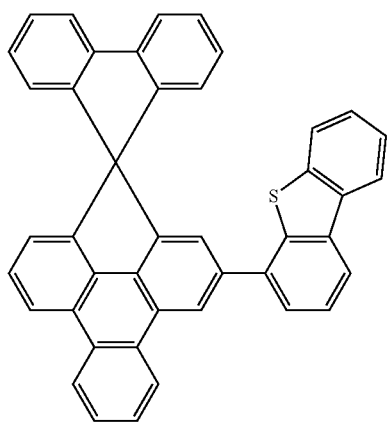

-continued
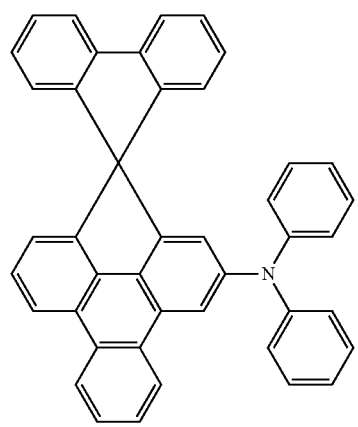
B15
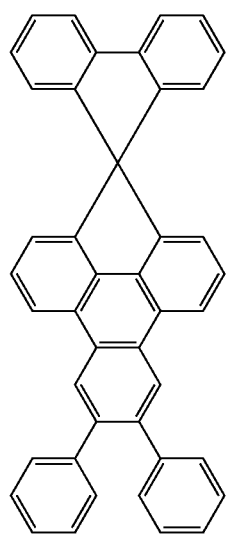
B16
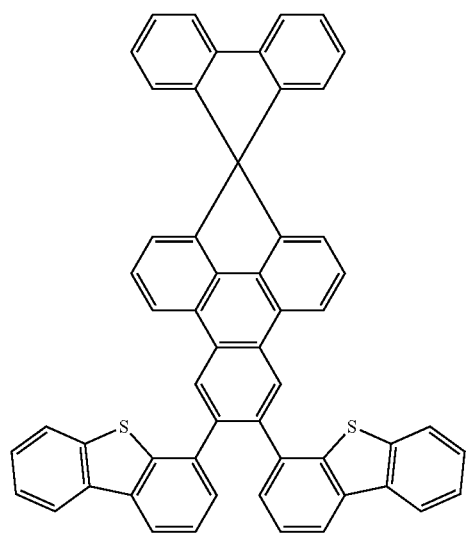
B17
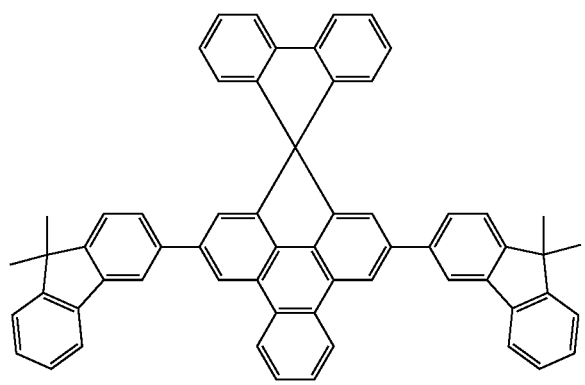
B18
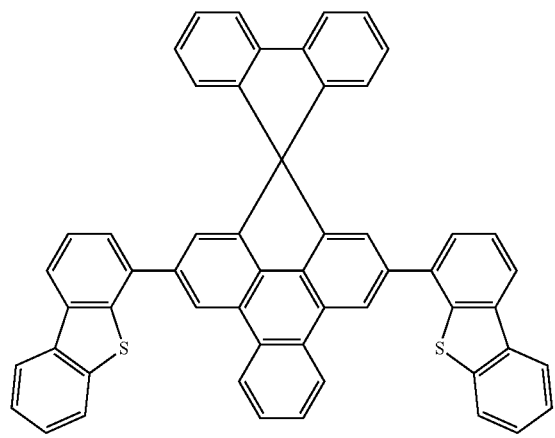
B19
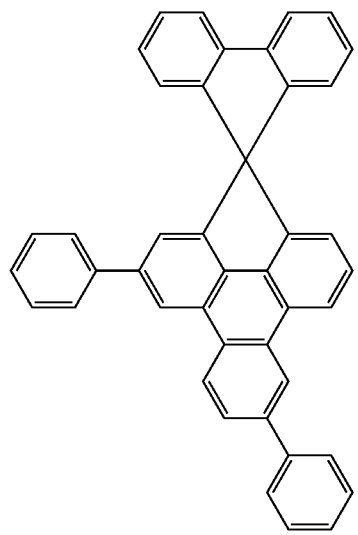
B20

-continued
B21
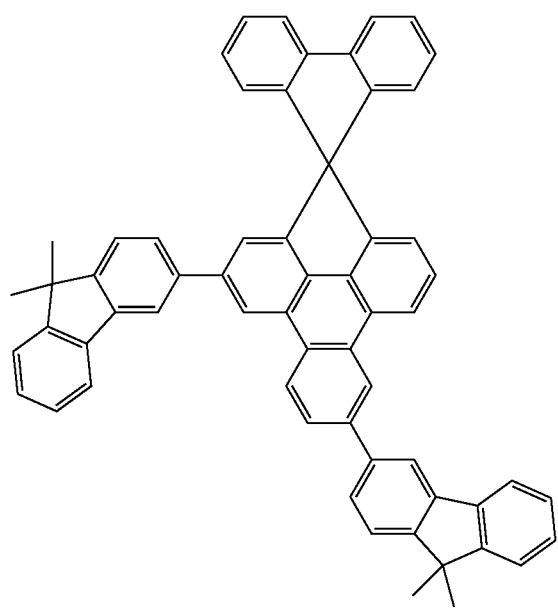
B22
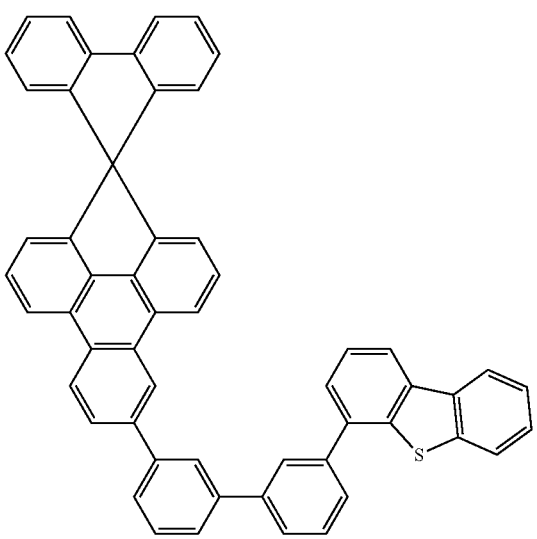
B23
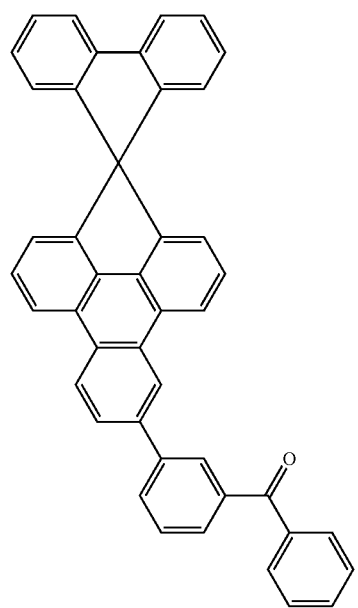
B24
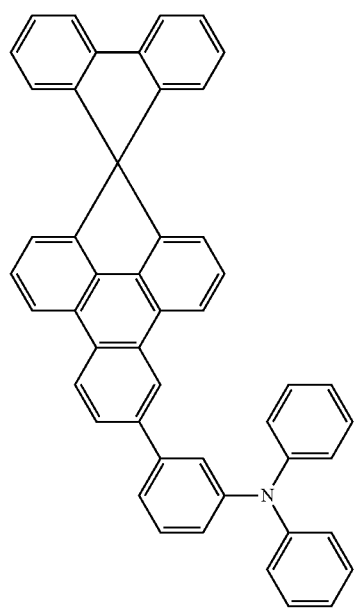

-continued
[Chem. 6]
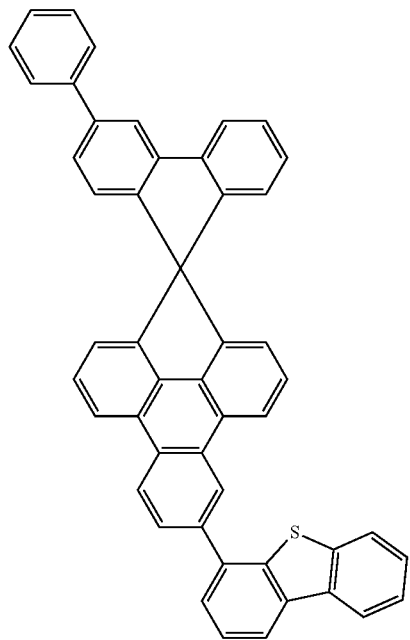
C01
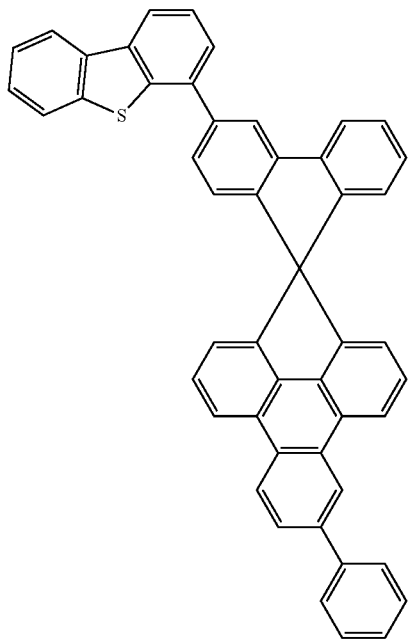
C02
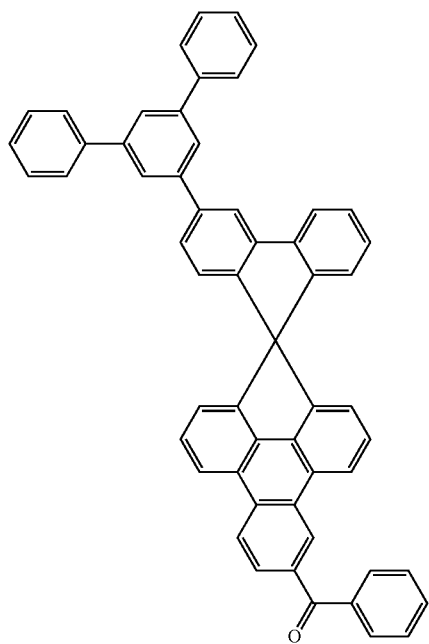
C03
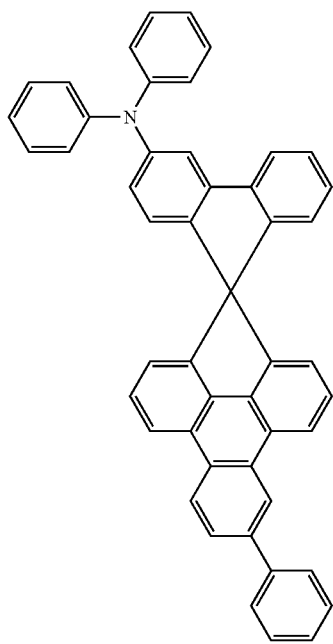
C04

-continued
C05
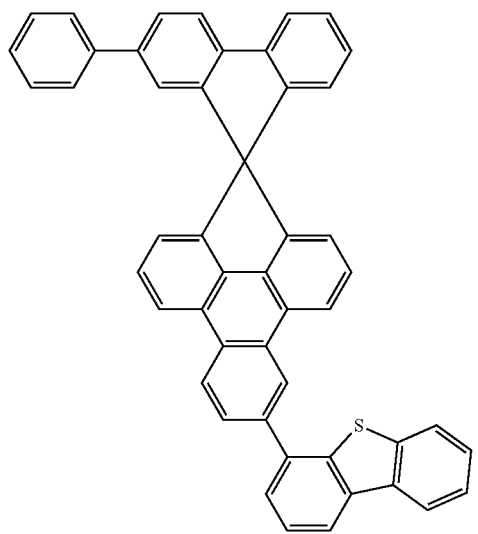
C06
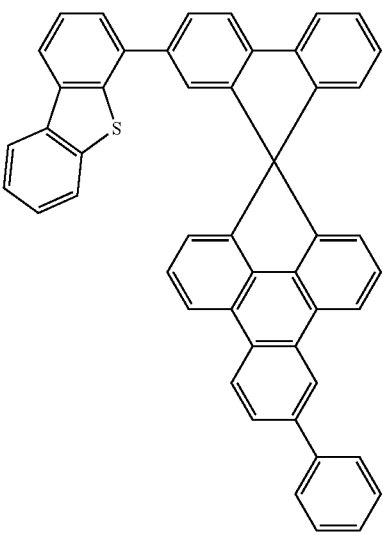
C07
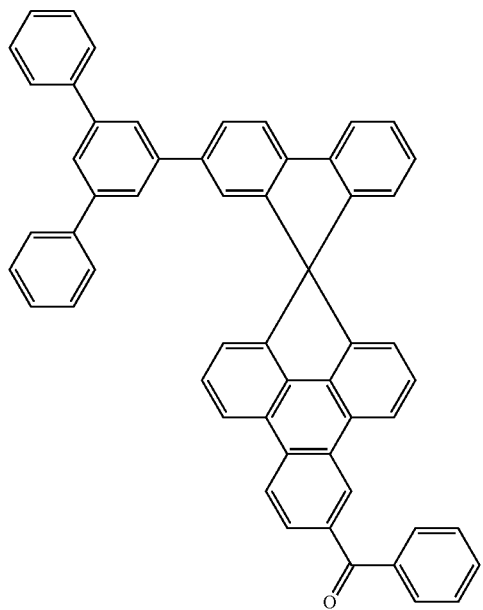
C08
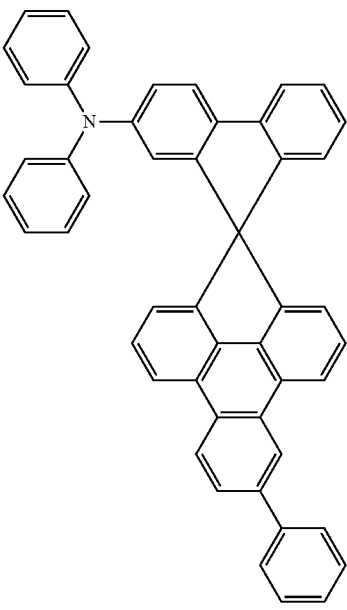
C09
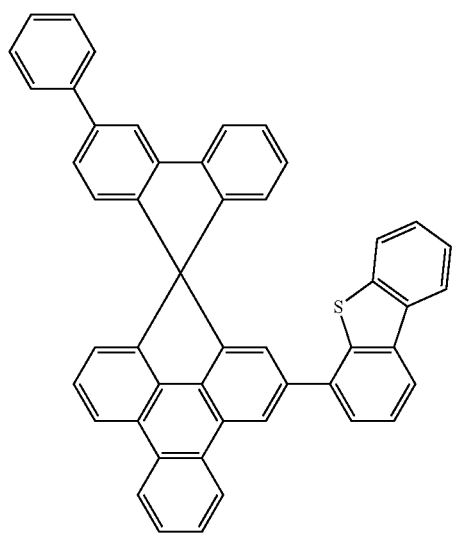
C10
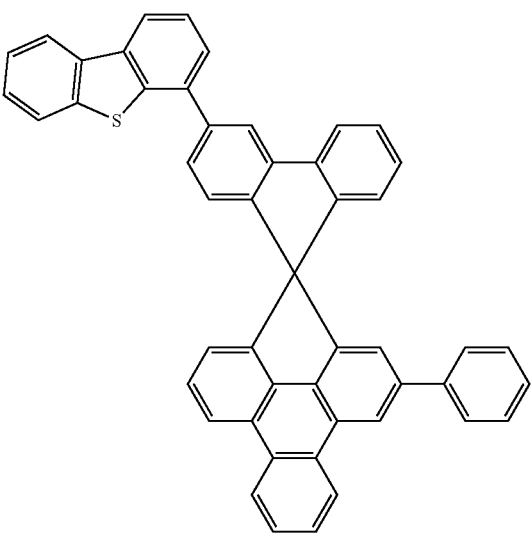

-continued
C11
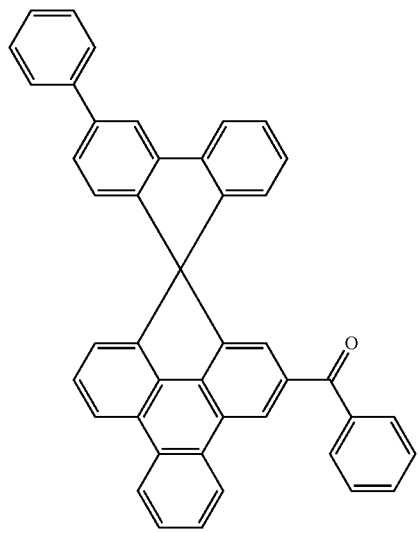
C12
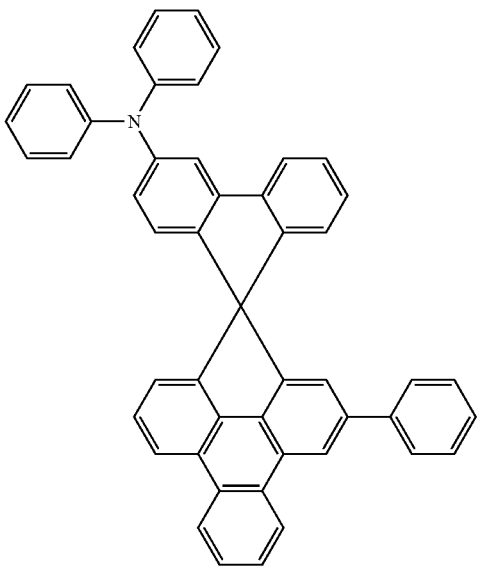
C13
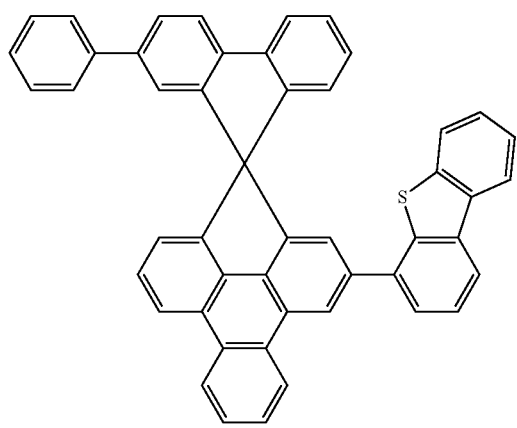
C14
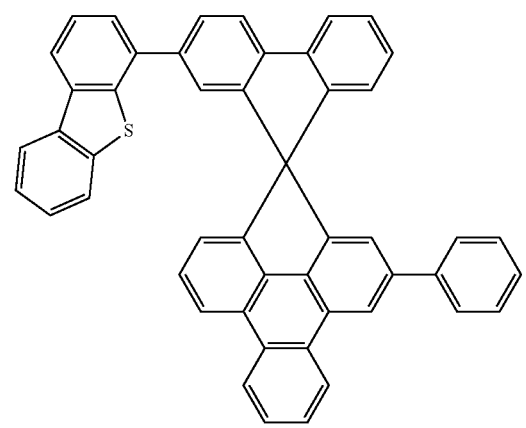
C15
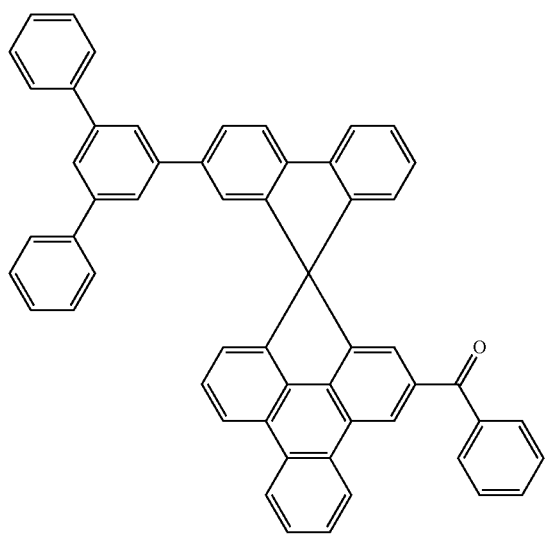
C16
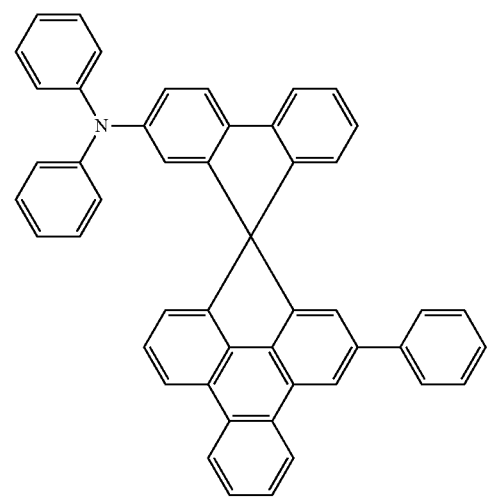

-continued
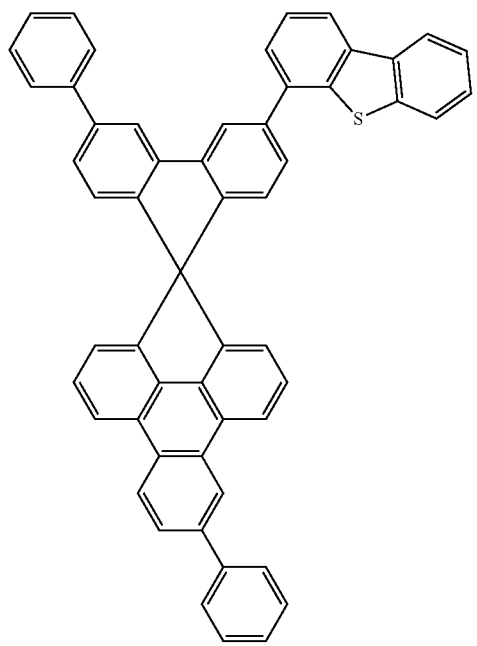
C17
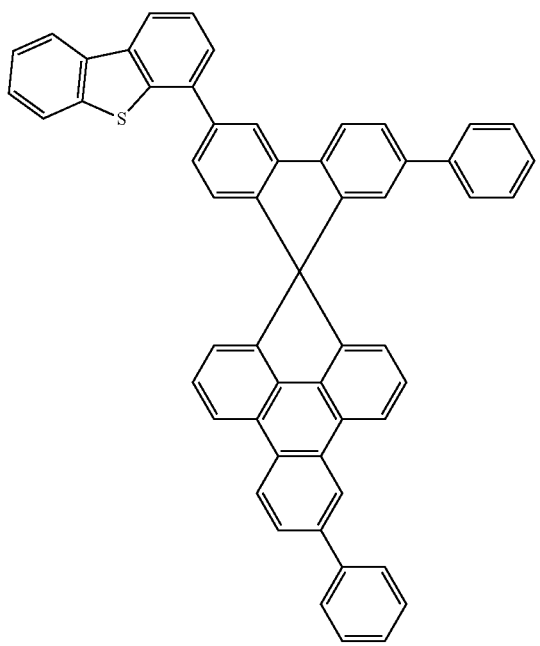
C18
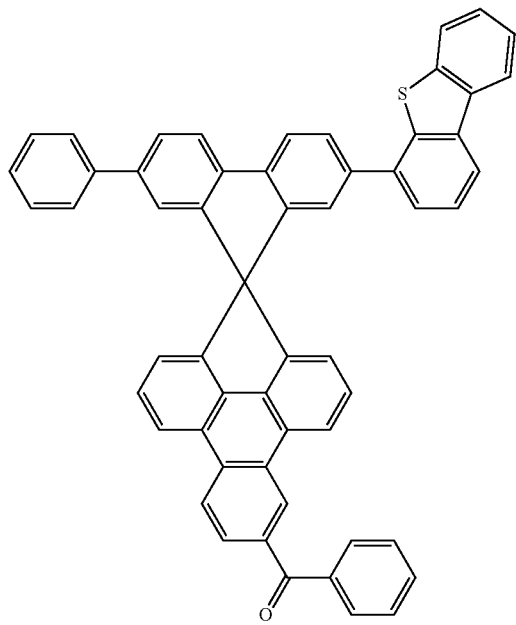
C19

[Chem. 7]
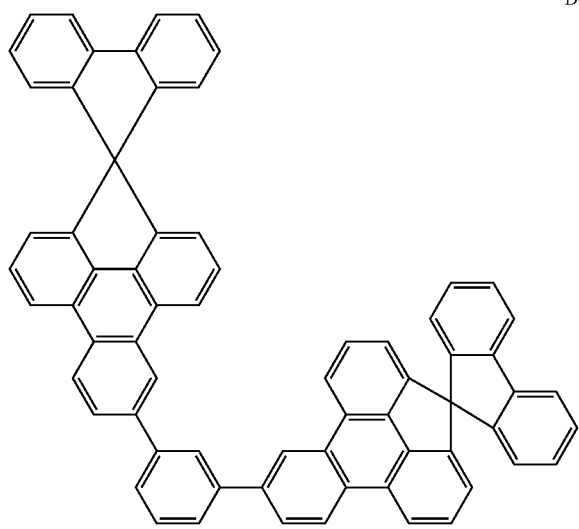
D01
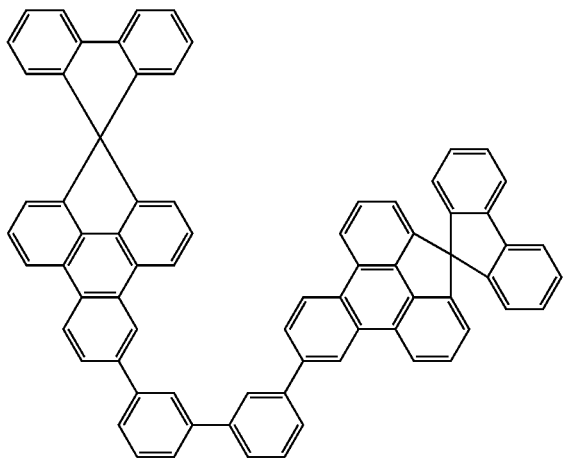
D02
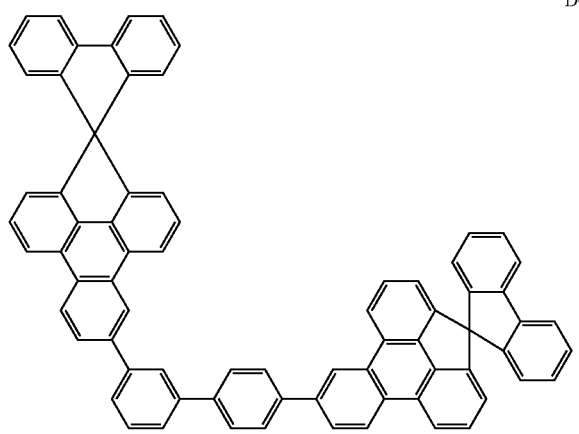
D03
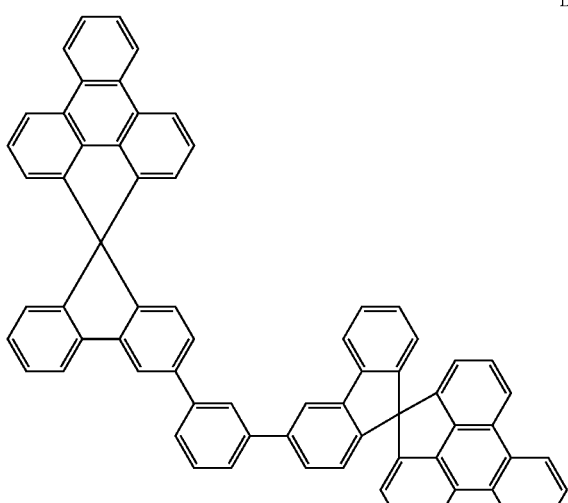
D04
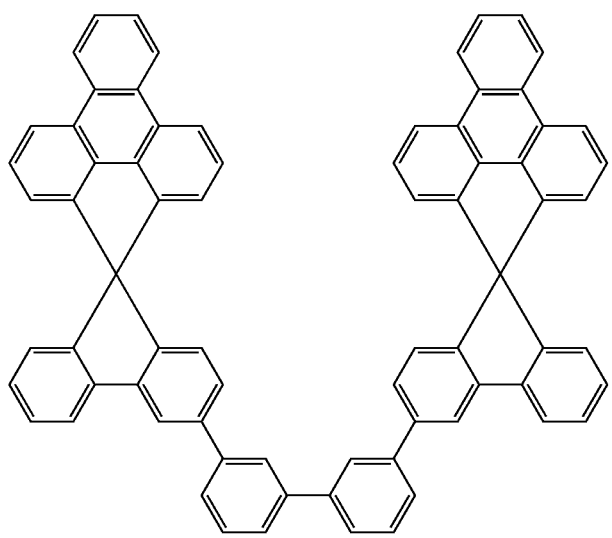
D05

-continued
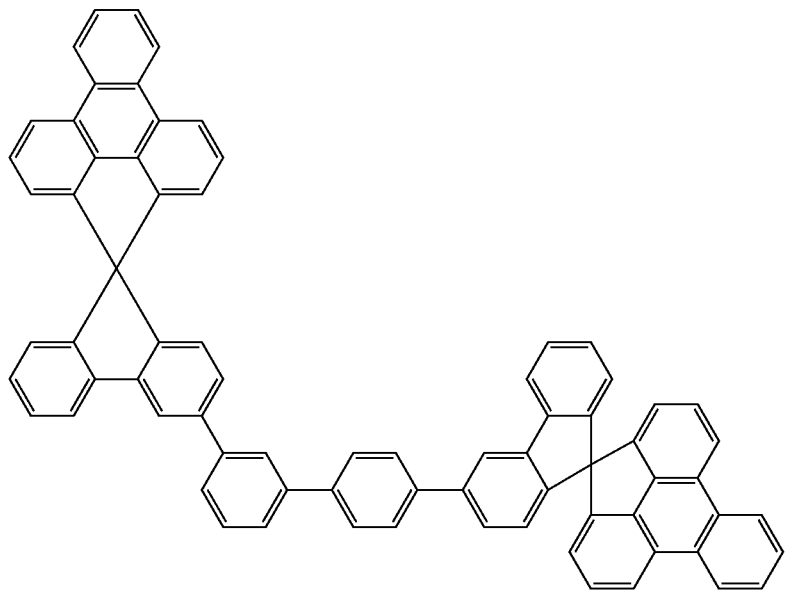
D06
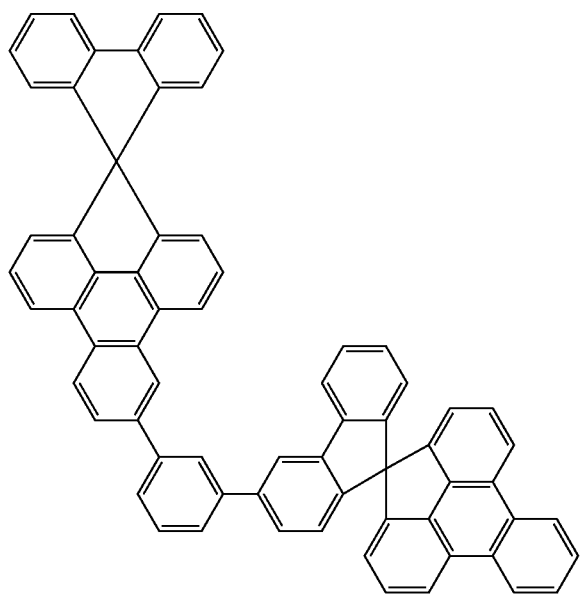
D07
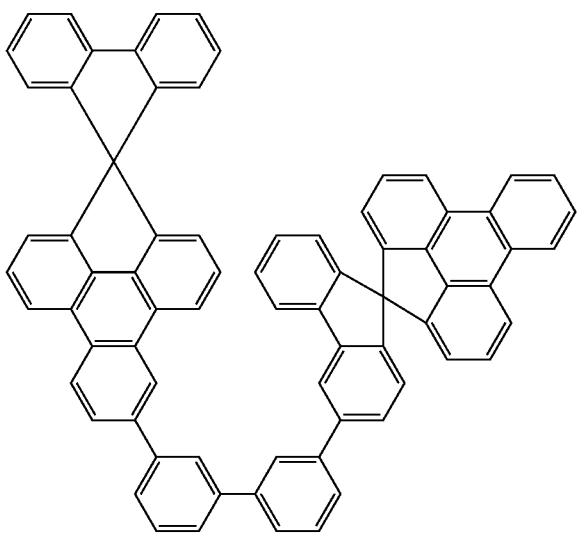
D08

D09

D10

D11

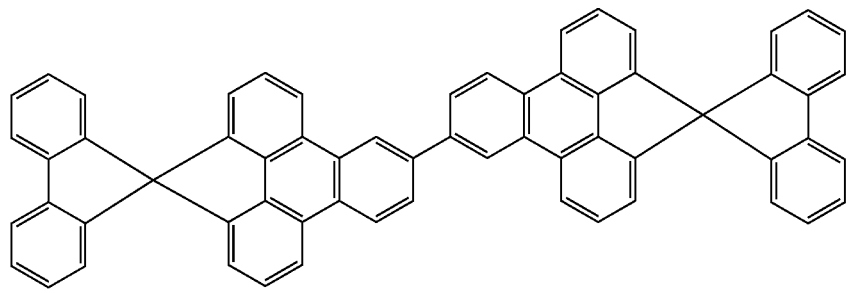

D12

The compounds shown in Group A among Example Compounds have substituents on the fluorene side. For example, Example Compound A03 has a substituent showing a large steric hindrance, and thereby the basic skeleton can have further reduced crystallinity. However, since the π-conjugated system is disconnected by the spiro bond, the characteristics of triphenylene, the high T1 energy level and the small difference between the S1 and T1 energy levels, can be maintained. That is, the substituent can provide a new function while maintaining the characteristics of the triphenylene group.

The compounds shown in Group B among Example Compounds have substituents on the triphenylene side and are thereby provided with steric hindrance of the substituent itself, in addition to the steric hindrance of the spiro structure.

By doing so, the crystallinity can be reduced compared to unsubstituted triphenylene.

As in the compounds of Group A, the π-conjugated system is disconnected by the spiro bond, and thereby the substituent can provide a new function while maintaining the characteristics of the triphenylene group.

The compounds shown in Group C among Example Compounds have substituents on both the fluorene group and the triphenylene group and thereby have properties of compounds in both Groups A and B. That is, both a new function provided by the substituent and a reduction in crystallinity of triphenylene can be achieved.

The compounds shown in Group D among Example Compounds have two basic skeletons of compounds according to the present invention. Since the glass transition temperature of the basic skeleton of compounds according to the present invention is high, 120° C., a compound having two basic skeletons also has a high glass transition temperature. That is, a material having a high film-forming property can be provided.

Among the compounds according to the present invention, in particular, compounds represented by the following General Formula [2] can be used:

[Chem. 8]

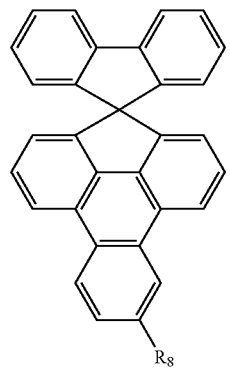

[2]

In General Formula [2], $R_8$ is any of a phenyl group, a biphenyl group, a terphenyl group, a naphthyl group, a phenanthryl group, a triphenylene group, a fluorenyl group, a dibenzothiophene group, a carbonyl group, an amino group, or a spiro[cyclopenta[def]triphenylene-4,9'-fluorene] group. In particular, $R_8$ can be a biphenyl group.

These substituents may have substituents selected from alkyl groups having 1 to 4 carbon atoms, substituted amino groups, dibenzothiophene groups, carbonyl groups having phenyl groups, and spiro[cyclopenta[def]triphenylene-4,9'-fluorene] groups.

Method of Synthesizing Spiro[Cyclopenta[def]Triphenylene-4,9'-Fluorene] Compound According to the Present Invention Next, a method of synthesizing a compound according to the present invention will be described.

Synthesis Example:

[Chem. 9]

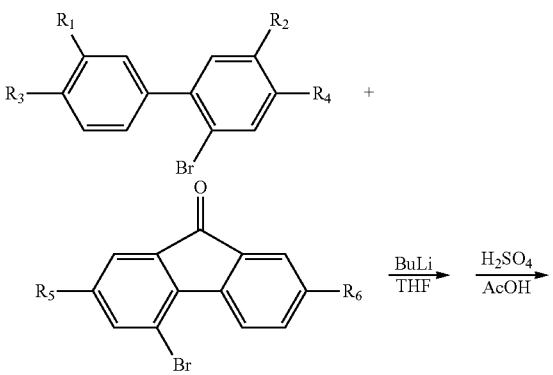

-continued

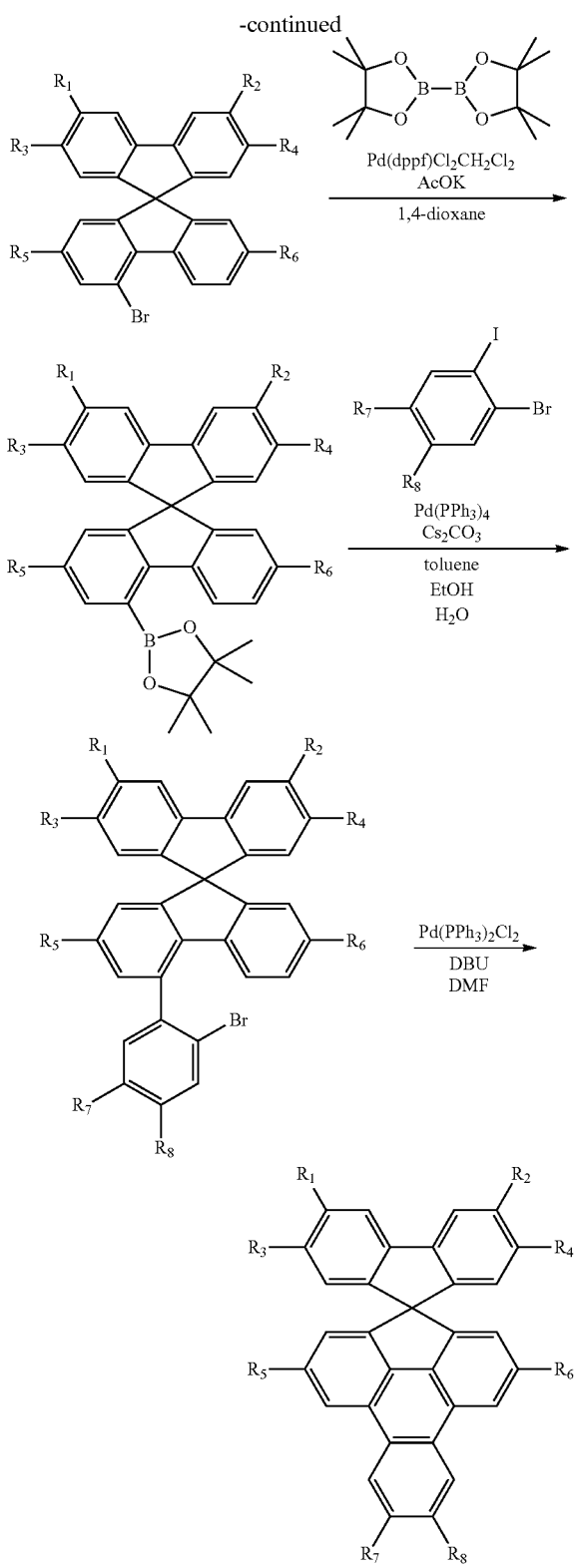

The compound according to the present invention is synthesized as in the above-mentioned synthesis example by forming a spiro bond between a bromobiphenyl derivative and a bromofluorenone derivative, then binding a iodobromobenzene derivative to the resulting product, and forming a triphenylene structure by a Mizoroki-Heck reaction. In the synthesis example, $R_1$ to $R_8$ are independently selected from the group consisting of hydrogen atoms, phenyl groups, biphenyl groups, terphenyl groups, naphthyl groups, phenanthryl groups, triphenylene groups, fluorenyl groups, dibenzothiophene groups, carbonyl groups, and amino groups.

A desired compound of the present invention can be synthesized by appropriately selecting a bromobiphenyl derivative, a bromofluorenone derivative, and an iodobromobenzene derivative in the above-mentioned reactions.

In the case of applying a compound according to the present invention to an organic light-emitting device, purification of the compound immediately before the application can be performed by sublimation. The purification effect of the sublimation is high for highly purifying organic compounds. However, in the sublimation purification, an organic compound having a larger molecular weight needs higher temperature and tends to be thermally decomposed in such high temperature.

Accordingly, the organic compound used in the organic light-emitting device can have a molecular weight of 1000 or less so that sublimation purification can be performed without excessive heating.

Organic Light-Emitting Device According to the Present Invention

An organic light-emitting device according to an embodiment of the present invention will be described below.

The organic light-emitting device according to this embodiment includes at least an anode and a cathode, as an example of a pair of electrodes facing each other, and an organic compound layer disposed between thereof. When the organic compound layer includes a light-emitting material, the layer serves as a light-emitting layer. The organic light-emitting device according to this embodiment includes a spiro[cyclopenta[def]triphenylene-4,9'-fluorene] compound represented by General Formula [1] in the organic compound layer.

The organic compound layer of the organic light-emitting device according to the embodiment may be a monolayer or a multilayer. The multilayer is a layer including those appropriately selected from, for example, a hole-injecting layer, a hole-transporting layer, a light-emitting layer, a hole-blocking layer, an electron-transporting layer, an electron-injecting layer, and an exciton-blocking layer. A plurality of layers selected from the above-mentioned layers may be used in combination.

The structure of the organic light-emitting device according to the embodiment is not limited to the above-mentioned ones, and various layer structures can be employed. For example, a structure having an insulating layer at the interface between an organic compound layer and an electrode, a structure having an adhesion layer or an interference layer, or a structure having an electron-transporting layer or a hole-transporting layer constituted of two layers having different ionization potentials can be employed.

The configuration of the device may be a top emission type, which extracts light from the electrode on the substrate side, or a bottom emission type, which extracts light on the opposite side of the substrate. Alternatively, a structure in which light is extracted from both sides can be employed.

The compound according to the present invention can be used in any layer structure as the organic compound layer of an organic light-emitting device and, in particular, can be used as the host material of a light-emitting layer.

The concentration of the host material of a light-emitting layer can be 50 wt % or more and 99.9 wt % or less, preferably 80 wt % or more and 99.9 wt % or less, based on the total weight of the light-emitting layer. The concentration of the guest material can be 0.01 wt % or more and 10 wt % or less in order to avoid concentration quenching.

The guest material may be uniformly contained in the entire layer of a host material or may be contained with concentration gradient or may be contained in a specific region of a host material layer so that the host material layer has a region not containing the guest material.

In the case of using the compound according to the present invention as the host material of a phosphorescent layer, the phosphorescent material used as the guest material is a metal complex such as an iridium complex, a platinum complex, a rhenium complex, a copper complex, a europium complex, or a ruthenium complex. In particular, the iridium complex, which has a strong phosphorescent property, can be used. The light-emitting layer may include a plurality of phosphorescent materials in order to assist transmission of excitons or carriers.

Specific examples of the iridium complex that is used as the phosphorescent material of the present invention are shown below, but the present invention is not limited thereto.

[Chem. 10]

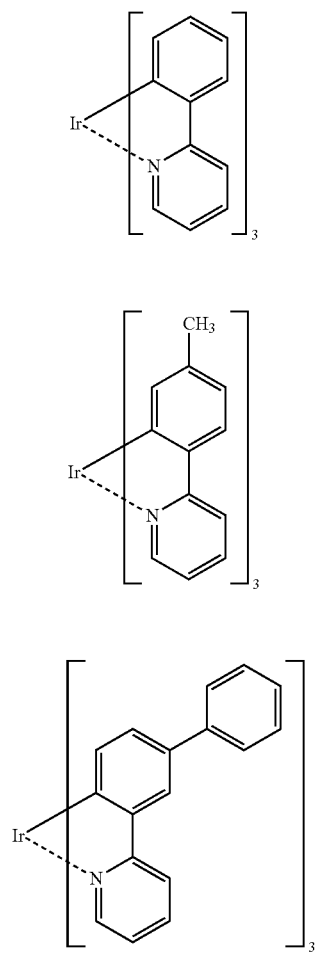

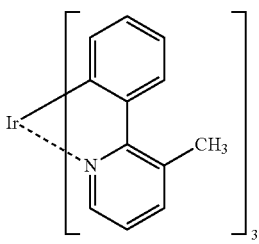

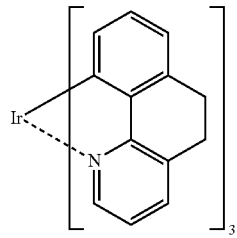

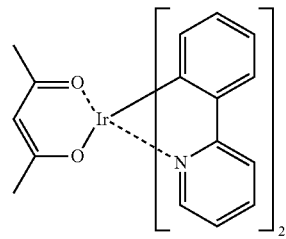

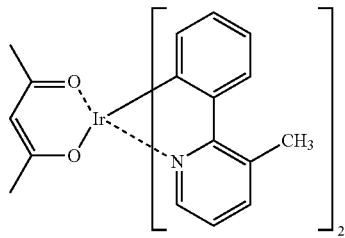

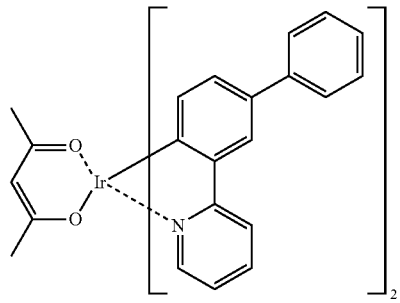

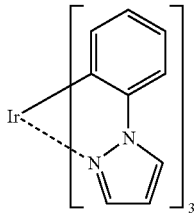

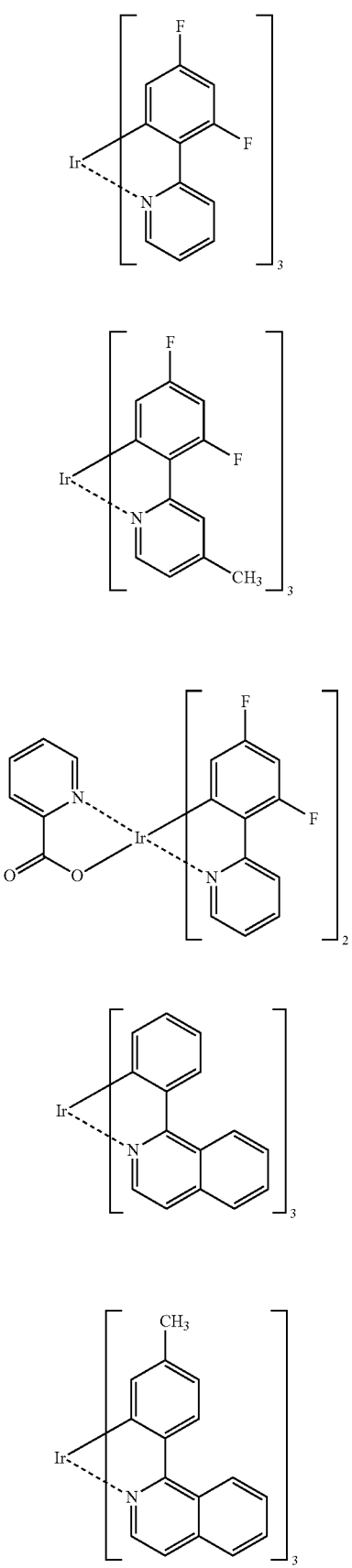
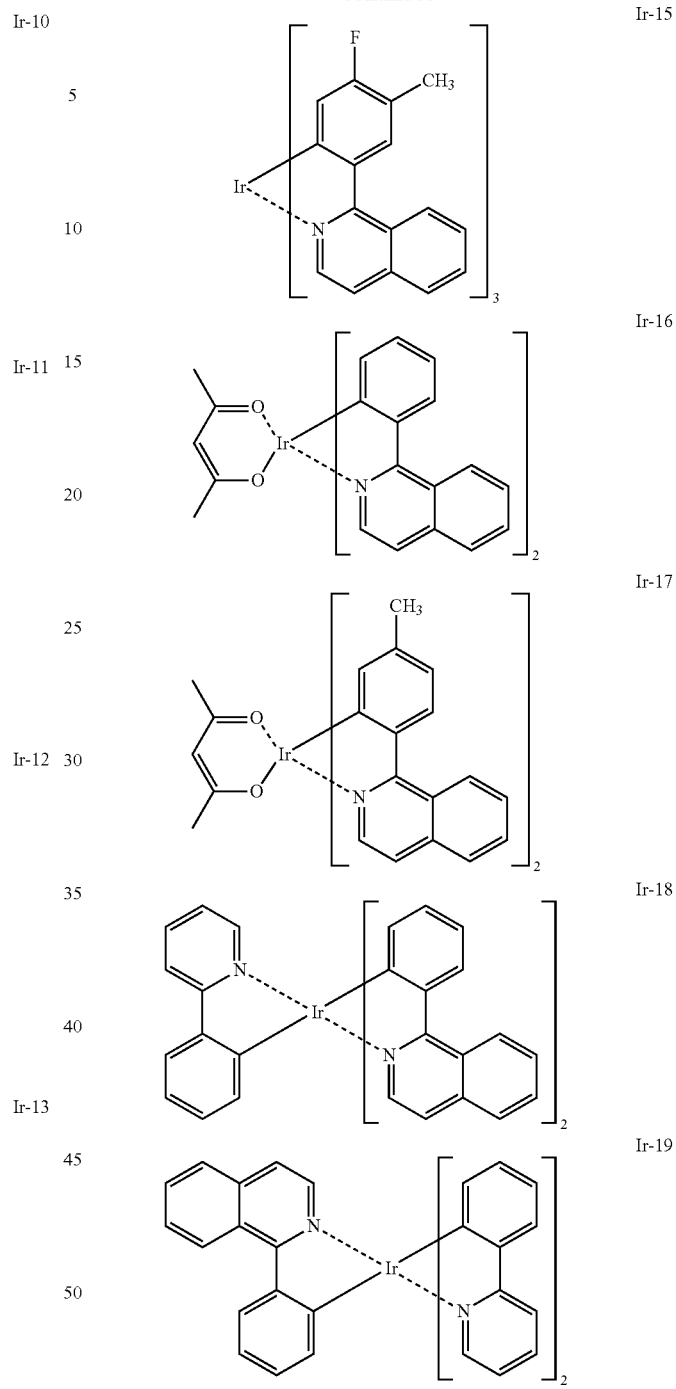

In addition to the compounds according to the present invention, known low-molecular-weight and high-molecular-weight compounds can be optionally used. More specifically, for example, a hole-injecting compound, a hole-transporting compound, a host material, a light-emitting compound, an electron-injecting compound, or an electron-transporting compound can be used together with the compound of the present invention.

Examples of these compounds will be described below.

The hole-injection/transporting material can be a material having a high hole mobility to facilitate the injection of holes from an anode and to transport the injected holes to a light-emitting layer. Examples of the low-molecular-weight and high-molecular-weight compounds having the hole-injection/transporting ability include triarylamine derivatives, phenylenediamine derivatives, stilbene derivatives, phthalocyanine derivatives, porphyrin derivatives, poly(vinylcarbazole), poly(thiophene), and other electrically conductive polymers.

Examples of the light-emitting material mainly relating to the emission function include, in addition to the above-mentioned phosphorescent guest materials and derivatives thereof, condensation compounds (e.g., fluorene derivatives, naphthalene derivatives, pyrene derivatives, perylene derivatives, tetracene derivatives, anthracene derivatives, and rubrene derivatives), quinacridone derivatives, coumarin derivatives, stilbene derivatives, organic aluminum complexes such as tris(8-quinolinolato)aluminum, organic beryllium complexes, and polymer derivatives such as poly(fluorene) derivatives and poly(phenylene) derivatives.

The electron injection/transporting material can be appropriately selected from those that facilitate the injection of electrons from a cathode and transport the injected electrons to a light-emitting layer, with consideration for the balance with the hole mobility of the hole injection/transporting material for example. Examples of the material having the electron injection/transporting ability include oxadiazole derivatives, oxazole derivatives, pyrazine derivatives, triazole derivatives, triazine derivatives, quinoline derivatives, quinoxaline derivatives, phenanthroline derivatives, and organic aluminum complexes.

As the anode material, a material having a large work function can be used. Examples of such materials include simple metals such as gold, platinum, silver, copper, nickel, palladium, cobalt, selenium, vanadium, and tungsten; alloys of these metals; metal oxides such as tin oxide, zinc oxide, indium oxide, indium tin oxide (ITO), and indium zinc oxide; and electrically conductive polymers such as polyaniline, polypyrrole, and polythiophene. These electrode materials can be used alone or in combination of two or more thereof. The anode may have either a monolayer or multilayer structure.

Meanwhile, as the cathode material, a material having a small work function can be used. Examples of such materials include alkali metals such as lithium; alkaline earth metals such as calcium; simple metals such as aluminum, titanium, manganese, silver, lead, and chromium; alloys of these simple metals such as magnesium-silver, aluminum-lithium, and aluminum-magnesium; and metal oxides such as indium tin oxide (ITO). These electrode materials can be used alone or in combination of two or more thereof. The cathode may have either a monolayer or multilayer structure.

In the organic light-emitting device according to the present invention, a layer containing the organic compound according to the present invention and a layer of another organic compound are thin films generally formed by vacuum deposition, ionic vapor deposition, sputtering, plasma CVD, or a known method of applying the compound dissolved in a suitable solvent (e.g., spin coating, dipping, casting, LB method, ink jet method). Particularly, in the layer formed by vacuum deposition or application of a solution, for example, crystallization hardly occurs to achieve high long-term stability. In the film formation by the application of a solution, the solution may additionally contain a suitable binder resin.

Examples of the binder resin include, but not limited to, polyvinylcarbazole resins, polycarbonate resins, polyester resins, ABS resins, acrylic resins, polyimide resins, phenol resins, epoxy resins, silicone resins, and urea resins. These binder resins may be singly used as a homopolymer or a copolymer or as a mixture of two or more of polymers. Furthermore, an additive such as a known plasticizer, antioxidant, or ultraviolet absorber may be optionally used.

Use of Organic Light-Emitting Device

The organic light-emitting device according to the present invention can be applied not only to a display or a lighting system, but also to an exposing light source of an electrographic image-forming apparatus or a backlight of a liquid crystal display.

The display includes the organic light-emitting device according to the embodiment in a display section. This display section includes a plurality of pixels. The pixel includes an organic light-emitting device according to the embodiment and a TFT device as an example of the switching device for controlling luminance, and the anode or the cathode of the organic light-emitting device is connected to the drain electrode or the source electrode of the TFT device. The display can be used as an image-displaying apparatus of, for example, a personal computer.

The display may be an image input apparatus that further includes an input section for inputting image information from, for example, an area CCD, a linear CCD, or memory card and outputs the input image to the display section. The display section of an image pickup apparatus or an ink-jet printer may have both an image output function for displaying image information input from the outside and an input function for inputting information processed into an image as an operation panel. The display may be used in a display section of a multi-functional printer.

Next, a display using the organic light-emitting device according to the embodiment will be described with reference to FIG. 2.

Figure 2:
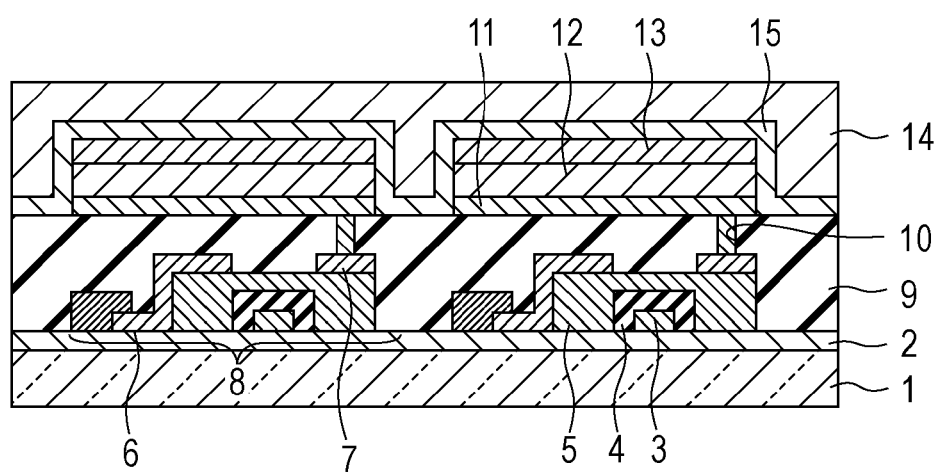
FIG. 2 is a schematic cross-sectional view illustrating organic light-emitting devices and switching devices connected to the organic light-emitting devices.

FIG. 2 is a schematic cross-sectional view of a display, illustrating organic light-emitting devices according to the embodiment and TFT devices as an example of the switching devices connected to the organic light-emitting devices. This figure shows two pairs of the organic light-emitting device and the TFT device. The details of the structure will be described below.

This display includes a substrate 1 such as a glass substrate and a moisture-proof film 2 disposed on the substrate 1 for protecting the TFT devices or the organic composition layer. Reference numeral 3 denotes a metal gate electrode, reference numeral 4 denotes a gate insulating film 4, and reference numeral 5 denotes a semiconductor layer.

The TFT device 8 includes a semiconductor layer 5, a drain electrode 6, and a source electrode 7. An insulating film 9 is disposed on the TFT device 8. The anode 11 of the organic light-emitting device and the source electrode 7 are connected via a contact hole 10. The display is not limited this configuration as long as either the anode or the cathode is connected to either the source electrode or the drain electrode of the TFT device.

In this drawing, the organic compound layer 12 of a multilayer is shown as one layer. Furthermore, a first protective layer 14 and a second protective layer 15 are disposed on the cathode 13 in order to inhibit deterioration of the organic light-emitting device.

The switching device of the display according to the embodiment is not particularly limited and may be a monocrystal silicon substrate, an MIM device, or an a-Si type device.

EXAMPLE 1

Synthesis of Example Compound D01

[Chem. 11]

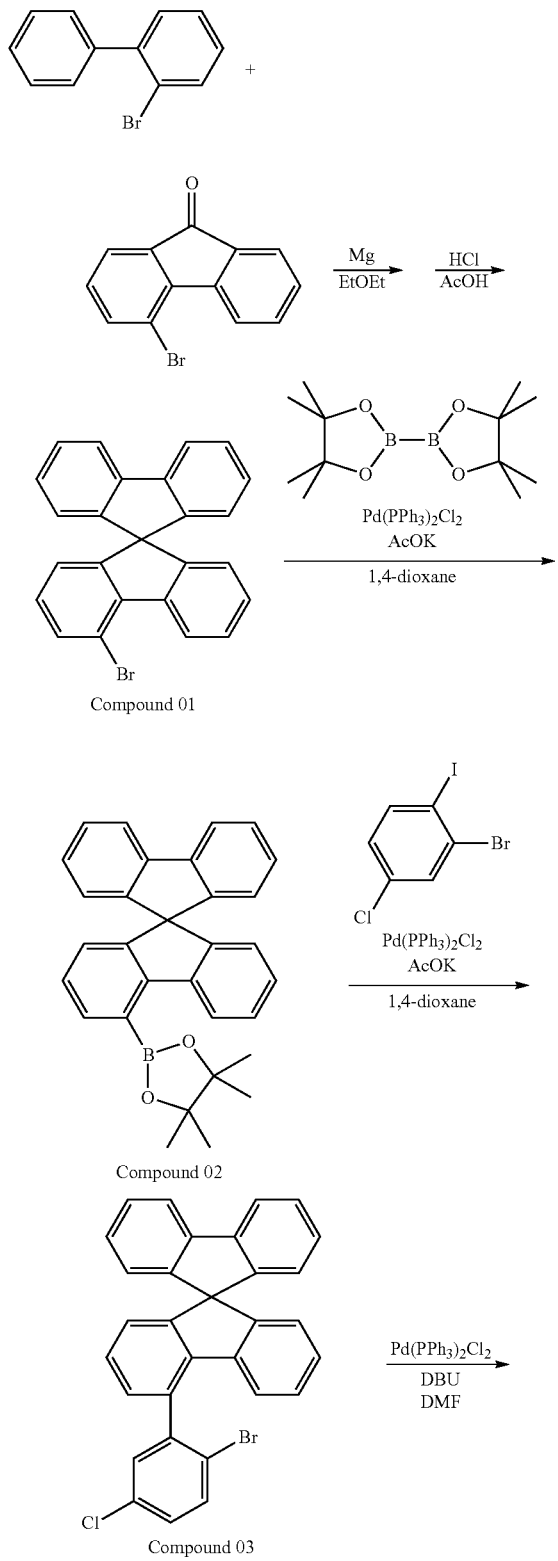

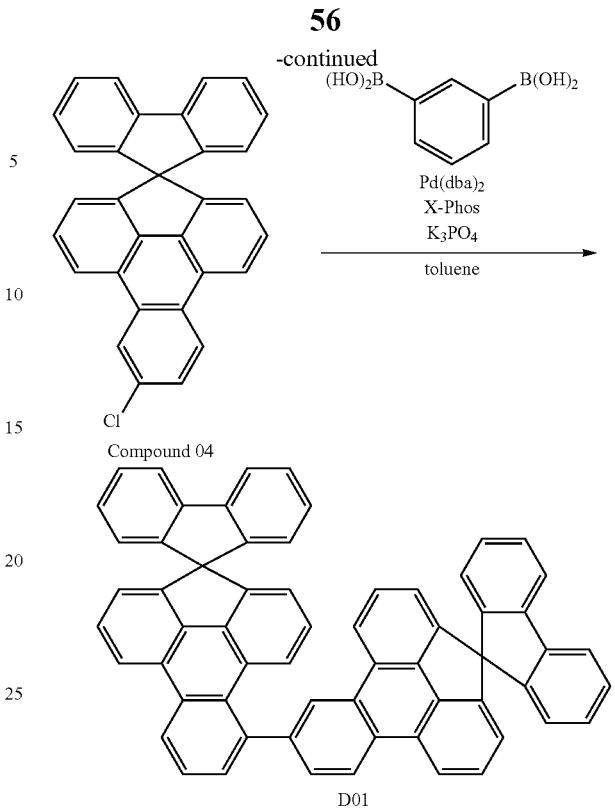

Synthesis of Compound 01

A Grignard reagent was prepared by putting 1.5 g (61.8 mmol) of magnesium in a reaction vessel, replacing the atmosphere inside the reaction vessel with argon, and then dropping 11.7 g (50.2 mmol) of 2-bromobiphenyl dissolved in 55 mL of dehydrated diethyl ether into the reaction vessel with stirring.

The following reagent and solvent:
dehydrated diethyl ether: 50 mL, and
2-bromofluorenone: 10 g (38.6 mmol) were put in another reaction vessel. The Grignard reagent prepared in advance was dropped into this reaction vessel, followed by stirring for 30 min. It was confirmed by thin layer chromatography that the raw materials disappeared, and instead, a new compound was produced.

The reaction solution was cooled to 0° C. and was subjected to extraction with a saturated ammonium chloride aqueous solution and ethyl acetate, and the organic layer was collected. After drying with sodium sulfate, the solvent was distilled off to obtain an intermediate of Compound 01.

The intermediate of Compound 01 and 200 mL of acetic acid were put in another reaction vessel. This reaction solution was heated to 120° C., and 20 mL of concentrated hydrochloric acid was dropped thereto over 10 min with stirring, followed by stirring at 120° C. for 1 hr. It was confirmed by thin layer chromatography that the raw materials disappeared, and instead, a new compound was produced.

The reaction vessel was cooled to 0° C., and the precipitate was collected and was washed with water and ethanol to obtain 13.0 g (33.1 mmol, yield: 85.8%) of Compound 01. The resulting compound was detected as a peak at m/z=394 by gas chromatography-mass spectrometer (GS-MS) and was thereby confirmed to be the target compound.

Synthesis of Compound 02

The following reagents:
dioxane: 140 mL,
Compound 01: 7.00 g (17.7 mmol),
bispinacolatodiboron: 6.75 g (26.6 mmol),
potassium acetate: 3.47 g (35.4 mmol), and bis(triphenylphosphine)palladium(II) dichloride: 621 mg (0.885 mmol)

were put in a reaction vessel. The reaction solution was stirred at 100° C. for 12 hr under a nitrogen atmosphere. It was confirmed by thin layer chromatography that the raw materials disappeared, and instead, a new compound was produced.

The reaction solution was cooled to room temperature and was then concentrated under reduced pressure, followed by purification by silica gel column chromatography (eluent: toluene/heptane=1:1). The target fraction was concentrated, followed by extraction with methanol to obtain 6.43 g (14.5 mmol, yield: 82.1%) of Compound 02. The resulting compound was detected as a peak at m/z=442 by matrix-assisted laser desorption/ionization time-of-flight mass spectrometry (MALDI-TOF MS) to confirm being the target compound.

Synthesis of Compound 03

The following reagents:
dioxane: 100 mL,
Compound 02: 5.00 g (11.3 mmol),
2-bromo-4-chloro-1-iodobenzene: 5.38 g (17.0 mmol),
potassium carbonate: 2.22 g (22.6 mmol), and
bis(triphenylphosphine)palladium(II) dichloride: 397 mg (0.565 mmol)

were put in a reaction vessel. This reaction solution was stirred at 100° C. for 24 hr under a nitrogen atmosphere. It was confirmed by gas chromatography-mass spectrometer (GS-MS) that the raw materials disappeared, and instead, a new compound was produced.

The reaction solution was cooled to room temperature and was then concentrated under reduced pressure, followed by purification by silica gel column chromatography (eluent: toluene/heptane=1:2). The target fraction was concentrated, followed by extraction with heptane and filtration of the precipitate to obtain 4.93 g (9.74 mmol, yield: 86.2%) of Compound 03. The resulting compound was detected as a peak at m/z =504 by gas chromatography-mass spectrometer (GS-MS) and was thereby confirmed to be the target compound.

Synthesis of Compound 04

The following reagents:
diazabicycloundecene: 10 g (65.7 mmol),
DMF: 10 mL,
Compound 03: 4.80 g (9.49 mmol), and
bis(triphenylphosphine)palladium(II) dichloride: 333 mg (0.474 mmol)

were put in a reaction vessel. This reaction solution was stirred at 170° C. for 5 hr under a nitrogen atmosphere. It was confirmed by gas chromatography-mass spectrometer (GS-MS) that the raw materials disappeared, and instead, the target compound was produced.

The reaction solution was cooled to room temperature and was then concentrated under reduced pressure, followed by purification by silica gel column chromatography (eluent: toluene/heptane=1:2). The target fraction was concentrated, followed by recrystallization from methanol to obtain 2.57 g (6.05 mmol, yield: 63.8%) of Compound 04. The resulting compound was detected as a peak at m/z =424 by gas chromatography-mass spectrometer (GS-MS) and was thereby confirmed to be the target compound.

Synthesis of Example Compound D01

The following reagents:
toluene: 30 mL,
Compound 04: 400 mg (0.941 mmol),
1,3-phenyleneboronic acid: 78.0 mg (0.471 mmol),
tripotassium phosphate: 400 mg (0.472 mmol),
bisdibenzylideneacetone palladium: 27.0 mg (0.0471 mmol), and
X-Phos(dicyclohexyl(2',4',6'-triisopropyl-[1,1'-biphenyl]-2-yl)phosphine): 67.3 mg (0.141 mmol)

were put in a reaction vessel. This reaction solution was stirred at 120° C. for 12 hr under a nitrogen atmosphere. It was confirmed by thin layer chromatography that the raw materials disappeared, and instead, a new compound was produced.

The reaction solution was cooled to room temperature and was then concentrated under reduced pressure, followed by purification by silica gel column chromatography (eluent: toluene/heptane=1:2). The target fraction was concentrated, followed by recrystallization from toluene/heptane and collection by filtration to obtain 170 mg (0.199 mmol, yield: 42.3%) of Example Compound D01. The resulting compound was detected as a peak at m/z =854 by matrix-assisted laser desorption/ionization time-of-flight mass spectrometry (MALDI-TOF MS) and was thereby confirmed to be the target compound. In $^1$H-NMR, 38 protons were attributed.

$^1$H-NMR (CDCl$_3$): δ (ppm)=9.03 (s,2H), 8.84 ppm (d,2H), 8.47 ppm (d,2H), 8.40 ppm (d,2H), 8.32 ppm (s,1H), 7.97-7.89 ppm (m,6H), 7.78 ppm (t,1H), 7.56 ppm (t,4H), 7.41 ppm (t,4H), 7.10 ppm (t,4H), 7.04 ppm (d,4H), 6.70 ppm (d,4H).

EXAMPLE 2

Synthesis of Example Compound B22

[Chem. 12]

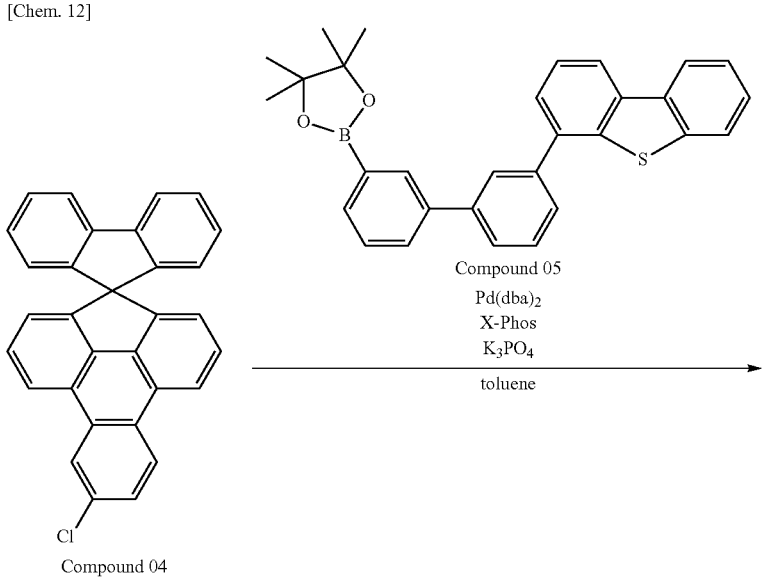

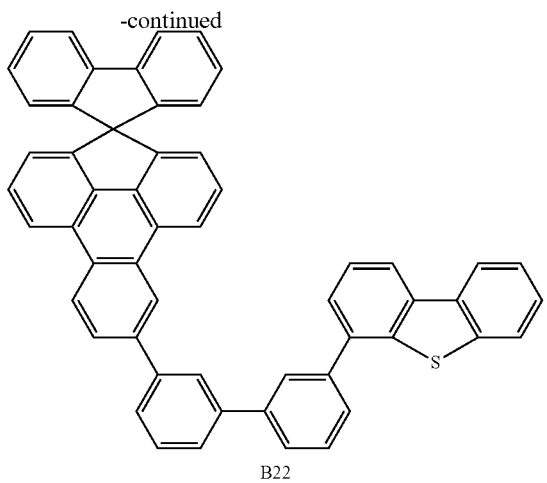
B22

In the same manner as the method of Example 1 except that Compound 05 was used instead of 1,3-phenyleneboronic acid in Example 1, 481 mg (0.663 mmol, yield: 70.5%) of Example Compound B22 was produced. The resulting compound was detected as a peak at m/z=724 by matrix-assisted laser desorption/ionization time-of-flight mass spectrometry (MALDI-TOF MS) and was thereby confirmed to be the target compound. In $^1$H-NMR, 32 protons were attributed.

$^1$H-NMR (CDCl$_3$): δ (ppm)=8.98 (s,1H), 8.78 ppm (d,1H), 8.44 ppm (d,1H), 8.36 ppm (d,1H), 8.22-8.16 ppm (m,4H), 8.08 ppm (d,1H), 7.93-7.77 ppm (m,7H), 7.66 ppm (t,2H), 7.61 ppm (d,2H), 7.57-7.40 ppm (m,6H), 7.10 ppm (t,2H), 7.03 ppm (d,2H), 6.70 ppm (d,2H).

EXAMPLE 3

Synthesis of Example Compound A09

[Chem. 13]

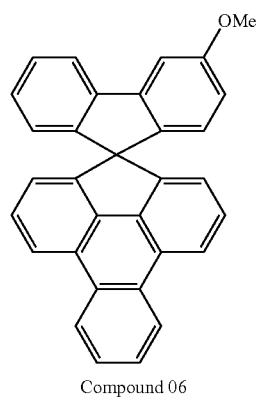
Compound 06

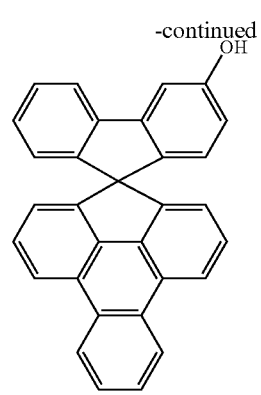
Compound 07

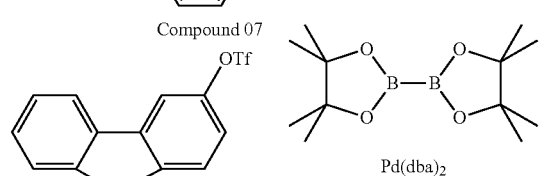
Compound 08

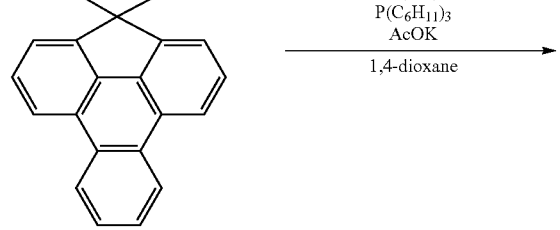

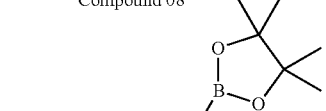

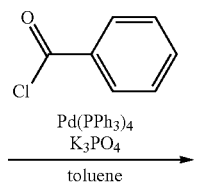
Compound 09

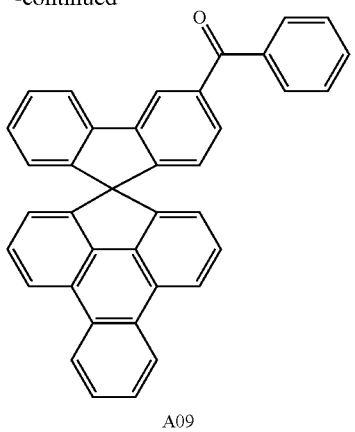

A09

Synthesis of Compound 06

Compound 06 was synthesized in the same manner as Example 1 except that 2-bromo-5-methoxybiphenyl and 2-bromo-1-iodobenzene were used instead of 2-bromophenyl and 2-bromo-4-chloro-1-iodobenzene, respectively, in Example 1.

Synthesis of Compound 07

The following reagents:

Compound 06: 1.17 g (2.78 mmol), and dichloromethane: 60 mL were put in a reaction vessel. This reaction solution was cooled to 0° C., followed by dropping of 3.40 mL (3.40 mmol) of a dichloromethane solution of boron tribromide (1 mol/L).

The reaction solution was warmed to room temperature and was stirred for 2 hr. It was confirmed by gas chromatography-mass spectrometer (GS-MS) that the raw materials disappeared, and instead, the target compound was produced. The reaction solution was extracted with toluene and an aqueous solution of sodium bicarbonate, and the organic layer was collected. After drying with sodium sulfate, the solvent was distilled off to obtain 1.06 g (2.60 mmol, yield: 93.4%) of Compound 07. The resulting compound was detected as a peak at m/z =406 by gas chromatography-mass spectrometer (GS-MS) and was thereby confirmed to be the target compound.

Synthesis of Compound 08

The following reagents:

Compound 07: 1.01 g (2.49 mmol), and pyridine: 30 mL were put in a reaction vessel. This reaction solution was cooled to 0° C., and 702 μL (4.17 mmol) of trifluoromethanesulfonic acid anhydride was dropped thereto, followed by stirring at room temperature for 2 hr. It was confirmed by thin layer chromatography that the raw materials disappeared, and instead, a new compound was produced. The solvent was concentrated under reduced pressure, followed by purification by silica gel column chromatography (eluent: toluene/heptane=1:2). The target fraction was concentrated, followed by recrystallization from methanol to obtain 1.26 g (2.34 mmol, yield: 94.1%) of Compound 08. The resulting compound was detected as a peak at m/z=538 by gas chromatography-mass spectrometer (GS-MS) and was thereby confirmed to be the target compound.

Synthesis of Compound 09

The following reagents:

dioxane: 50 mL,

Compound 08: 1.03 g (1.91 mmol), bispinacolatodiboron: 729 mg (2.87 mmol), potassium acetate: 375 mg (3.82 mmol), bis(dibenzylideneacetone)palladium: 54.9 mg (0.0955 mmol), and tricyclohexylphosphine: 80.3 mg (0.287 mmol)

were put in a reaction vessel. This reaction solution was stirred at 100° C. for 12 hr under a nitrogen atmosphere. It was confirmed by thin layer chromatography that the raw materials disappeared, and instead, a new compound was produced. The reaction solution was cooled to room temperature and was then concentrated under reduced pressure, followed by purification by silica gel column chromatography (eluent: toluene/heptane=1:1). The target fraction was concentrated, followed by extraction with methanol and filtration to obtain 704 mg (1.36 mmol, yield: 71.4%) of Compound 09. The resulting compound was detected as a peak at m/z=516 by matrix-assisted laser desorption/ionization time-of-flight mass spectrometry (MALDI-TOF MS) and was thereby confirmed to be the target compound.

Synthesis of Example Compound A09

The following reagents:

toluene: 30 mL,

Compound 09: 500 mg (0.968 mmol), benzoyl chloride: 272 mg (1.94 mmol), and tripotassium phosphate: 411 mg (1.94 mmol), and tetrakistriphenylphosphine palladium: 55.9 mg (0.0484 mmol)

were put in a reaction vessel. This reaction solution was stirred at 90° C. for 12 hr under a nitrogen atmosphere. It was confirmed by thin layer chromatography that the raw materials disappeared, and instead, a new compound was produced. The reaction solution was cooled to room temperature and was then concentrated under reduced pressure, followed by purification by silica gel column chromatography (eluent: toluene/heptane=1:2). The target fraction was concentrated, followed by recrystallization from toluene/heptane and filtration to obtain 389 mg (0.787 mmol, yield: 81.3%) of Example Compound A09. The resulting compound was detected as a peak at m/z =494 by matrix-assisted laser desorption/ionization time-of-flight mass spectrometry (MALDI-TOF MS) and was thereby confirmed to be the target compound.

EXAMPLE 4

Synthesis of Example Compound A10

[Chem. 14]

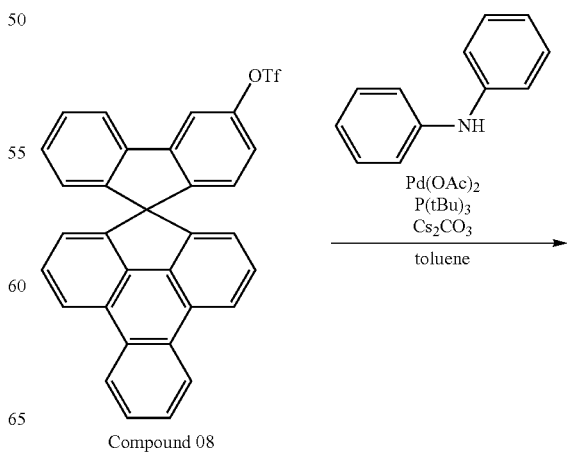

Compound 08

-continued

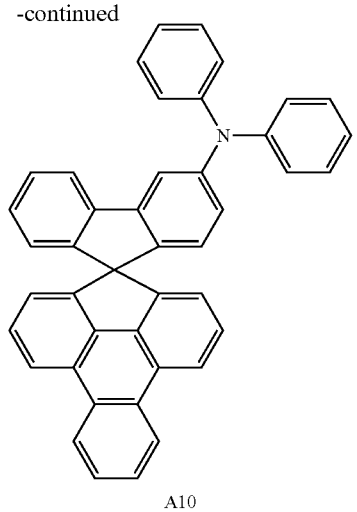

A10

The following reagents:
toluene: 30 mL,
Compound 08: 520 mg (0.968 mmol),
diphenylamine: 328 mg (1.94 mmol),
cesium carbonate: 632 mg (1.94 mmol),
palladium acetate: 10.9 mg (0.0484 mmol), and
tri-tert-butylphosphine: 19.6 mg (0.0968 mmol)
were put in a reaction vessel. This reaction solution was stirred at 110° C. for 12 hr under a nitrogen atmosphere. It was confirmed by thin layer chromatography that the raw materials disappeared, and instead, a new compound was produced. The reaction solution was cooled to room temperature and was then concentrated under reduced pressure, followed by purification by silica gel column chromatography (eluent: toluene/heptane=1:1). The target fraction was concentrated, followed by recrystallization from toluene/heptane and filtration to obtain 389 mg (0.697 mmol, yield: 72.0%) of Example Compound A10. The resulting compound was detected as a peak at m/z=557 by matrix-assisted laser desorption/ionization time-of-flight mass spectrometry (MALDI-TOF MS) and was thereby confirmed to be the target compound.

EXAMPLE 5

Example Compound B22 was measured for triplet energy by the following method. The phosphorescence spectrum of a diluted solution of Example Compound B08 in toluene was measured under a nitrogen atmosphere at 77 K at an excitation wavelength of 300 nm using a spectrophotofluorometer (manufactured by Hitachi, Ltd., F-4500). The triplet energy level determined from the peak wavelength on the shortest wavelength side in the resulting phosphorescence spectrum was 2.66 eV (467 nm).

Then, Example Compound B22 was measured for singlet energy by the following method. The absorption spectrum of a diluted solution of the compound in dichloromethane was measured using an ultraviolet and visible spectrophotometer (manufactured by JASCO Corp., V-560). The singlet energy level determined from the absorption edge of the resulting absorption spectrum was 3.42 eV (363 nm). Thus, the difference between the singlet and triplet energy levels was 0.76 eV.

The glass transition temperature of Example Compound B22 was further measured using a differential scanning calorimeter (manufactured by NETZSCH GmbH, DSC204F1) and was 172° C.

EXAMPLE 6

Example Compound D01 was subjected to the same measurements as in Example Compound of Example 5 to give a single energy level of 3.42 eV (363 nm), a triplet energy level of 2.64 eV (470 nm), a difference between the singlet and triplet energy levels of 0.78 eV, and a glass transition temperature of 256° C.

COMPARATIVE EXAMPLE 1

[Chem. 15]

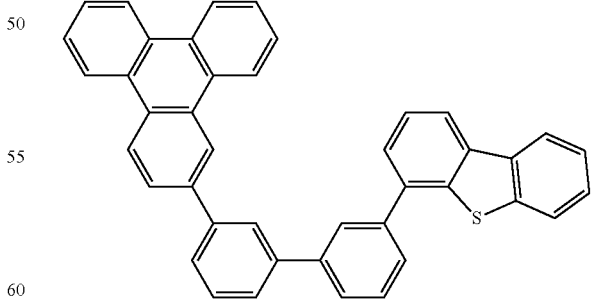

Comparative Compound 01

Comparative Compound 01 was subjected to the same measurements as in Example Compound of Example 5 to give a glass transition temperature of 108° C.

The measured results are shown in Table 3.

TABLE 3

| | Structural formula | Singlet energy | Triplet energy | Energy difference between singlet and triplet states | Glass transition temperature |
|---|---|---|---|---|---|
| Example Compound D01 | | 3.42 eV | 2.64 eV | 0.78 eV | 256° C. |
| Example Compound B22 | | 3.42 eV | 2.66 eV | 0.76 eV | 172° C. |
| Comparative Compound 01 | | — | — | — | 108° C. |

The difference between the singlet and triplet energy levels was 0.78 eV in Example Compound D01 and was 0.76 eV in Example Compound B22. These values are similar to the value, 0.64 eV, of the basic skeleton of the present invention.

The glass transition temperature of Example Compound B22 having one basic skeleton of compounds according to the present invention was 172° C., and that of Example Compound D01 having two basic skeletons of compounds according to the present invention was 256° C. Thus, it was revealed that the glass transition temperature was increased with an increase in number of the basic skeletons of compounds according to the present invention.

The glass transition temperature of Comparative Compound 01, which was different from Example Compound B22 in that the basic skeleton was triphenylene, was 108° C. Thus, it was revealed that a compound having the basic skeleton of compounds according to the present invention had a high glass transition temperature.

EXAMPLE 7

In this example, an organic light-emitting device having a configuration of anode/hole-transporting layer/light-emitting layer/hole-blocking layer/electron-transporting layer/cathode disposed in this order on a substrate was produced by the following method.

A film of ITO was formed on a glass substrate by sputtering as an anode having a thickness of 120 nm, and the resulting product was used as a transparent electrically conductive support substrate (ITO substrate). On this ITO substrate, an organic compound layers and electrode layers shown below were successively formed by resistance heating vacuum vapor deposition in a vacuum chamber of $10^{-5}$ Pa. On this occasion, the area of electrodes facing each other was adjusted to be 3 mm². The layers were:

hole-transporting layer (40 nm): HTL-1, light-emitting layer (30 nm): Example Compound B22 (70 wt %), HBL-1 (20 wt %), and Ir-1 (10 wt %), hole-blocking layer (10 nm): HBL-1, electron-transporting layer (30 nm): ETL-1, metal electrode layer 1 (0.5 nm): LiF, and metal electrode layer 2 (100 nm): Al.

[Chem. 16]

HTL-1

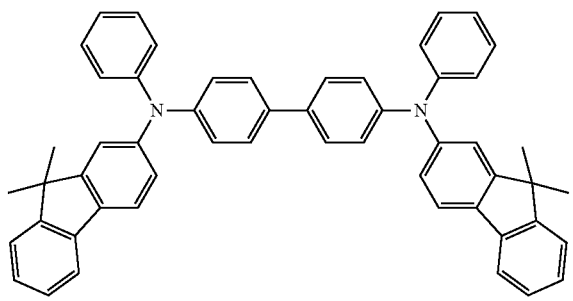

HBL-1

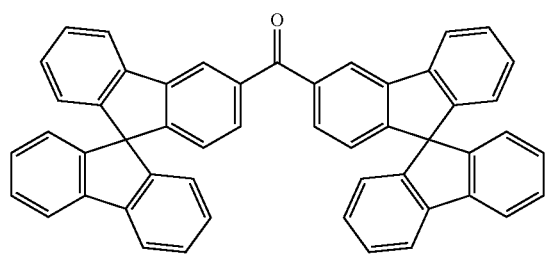

ETL-1

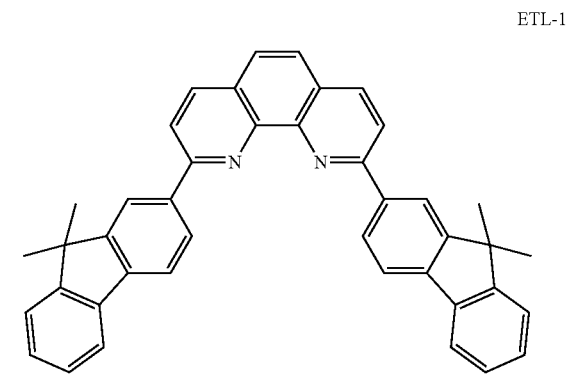

Ir-01

HOST-1

HOST-2

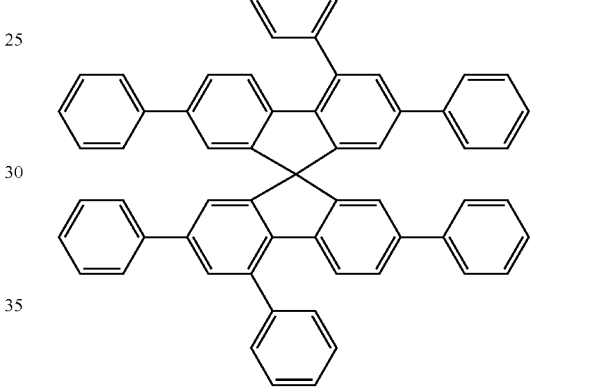

Then, in order to prevent deterioration of the organic light-emitting device due to absorption of moisture, covering with a protective glass plate and sealing with an acrylic polymer adhesive were performed in a dried air atmosphere. Thus, an organic light-emitting device was produced.

A voltage of 5.4 V was applied to the resulting organic light-emitting device using the ITO electrode as a positive electrode and the Al electrode as the negative electrode to observe green light emission with a luminous efficiency of 63 cd/A and a luminance of 4000 cd/m².

EXAMPLE 8

A light-emitting device was produced in the same manner as the method of Example 7 using the following materials:

hole-transporting layer (40 nm): HTL-1, light-emitting layer (30 nm): Example Compound D01 (70 wt %), HBL-1 (20 wt %), and Ir-1 (10 wt %), hole-blocking layer (10 nm): HBL-1, electron-transporting layer (30 nm): ETL-1, metal electrode layer 1 (0.5 nm): LiF, and metal electrode layer 2 (100 nm): Al.

A voltage of 5.2 V was applied to the resulting device to observe green light emission with a luminous efficiency of 58 cd/A and a luminance of 4000 cd/m².

EXAMPLE 9

A light-emitting device was produced in the same manner as the method of Example 7 using the following materials:
hole-transporting layer (40 nm): HTL-1,
light-emitting layer (30 nm): HOST-1 (70 wt %), Example Compound A09 (20 wt %), and Ir-1 (10 wt %),
hole-blocking layer (10 nm): Example Compound A09,
electron-transporting layer (30 nm): ETL-1,
metal electrode layer 1 (0.5 nm): LiF, and
metal electrode layer 2 (100 nm): Al.

A voltage of 5.8 V was applied to the resulting device to observe green light emission with a luminous efficiency of 70 cd/A and a luminance of 4000 cd/m$^2$.

EXAMPLE 10

A light-emitting device was produced in the same manner as the method of Example 7 using the following materials:
hole-transporting layer (40 nm): Example Compound A10,
light-emitting layer (30 nm): HOST-1 (70 wt %), HBL-1 (20 wt %), and Ir-1 (10 wt %),
hole-blocking layer (10 nm): HBL-1,
electron-transporting layer (30 nm): ETL-1,
metal electrode layer 1 (0.5 nm): LiF, and
metal electrode layer 2 (100 nm): Al.

A voltage of 5.7 V was applied to the resulting device to observe green light emission with a luminous efficiency of 68 cd/A and a luminance of 4000 cd/m$^2$.

COMPARATIVE EXAMPLE 2

A light-emitting device was produced in the same manner as the method of Example 7 using the following materials:
hole-transporting layer (40 nm): HTL-1,
light-emitting layer (30 nm): HOST-1 (70 wt %), HBL-1 (20 wt %), and Ir-1 (10 wt %),
hole-blocking layer (10 nm): HBL-1,
electron-transporting layer (30 nm): ETL-1,
metal electrode layer 1 (0.5 nm): LiF, and
metal electrode layer 2 (100 nm): Al.

A voltage of 6.0 V was applied to the resulting device to observe green light emission with a luminous efficiency of 57 cd/A and a luminance of 4000 cd/m$^2$.

COMPARATIVE EXAMPLE 3

A light-emitting device was produced in the same manner as the method of Example 7 using the following materials:
hole-transporting layer (40 nm): HTL-1,
light-emitting layer (30 nm): HOST-2 (70 wt %), HBL-1 (20 wt %), and Ir-1 (10 wt %),
hole-blocking layer (10 nm): HBL-1,
electron-transporting layer (30 nm): ETL-1,
metal electrode layer 1 (0.5 nm): LiF, and
metal electrode layer 2 (100 nm): Al.

A voltage of 6.5 V was applied to the resulting device to observe green light emission with a luminous efficiency of 50 cd/A and a luminance of 4000 cd/m2.

Table 4 shows the results above. The light-emitting layer host is the component having the largest weight ratio in the light-emitting layer.

TABLE 4

| | Hole-transporting layer | Light-emitting layer host | Hole-blocking layer | Applied voltage 4000 cd/m$^2$ (V) | Luminous efficiency 4000 cd/m$^2$ (cd/A) |
|---|---|---|---|---|---|
| Example 7 | HTL-1 | Example Compound B22 | HBL-1 | 5.4 | 63 |
| Example 8 | HTL-1 | Example Compound D01 | HBL-1 | 5.2 | 58 |
| Example 9 | HTL-1 | HOST-1 | Example Compound A09 | 5.8 | 70 |
| Example 10 | Example Compound A10 | HOST-1 | HBL-1 | 5.7 | 68 |
| Comparative Example 2 | HTL-1 | HOST-1 | HBL-1 | 6.0 | 57 |
| Comparative Example 3 | HTL-1 | HOST-2 | HBL-1 | 6.5 | 50 |

As described above, the compounds of the present invention are materials having small differences between the singlet and triplet energy levels and showing high glass transition temperatures. Organic light-emitting devices including the compounds can have low driving voltages and high luminous efficiencies.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-241203, filed Oct. 27, 2010, and Japanese Patent Application No. 2011-159077, filed Jul. 20, 2011, which are hereby incorporated by reference herein in their entirety.

REFERENCE SIGNS LIST

8 TFT device
11 anode
12 organic compound layer
13 cathode

The invention claimed is:
1. A spiro[cyclopenta[def]triphenylene-4,9'-fluorene] compound represented by the following General Formula [1]:

[Chem. 1]

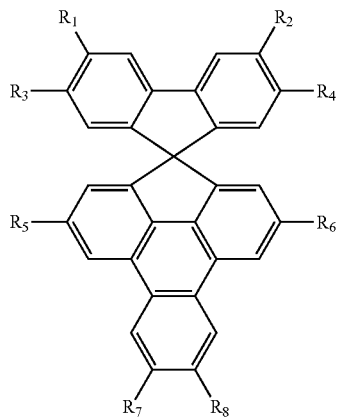

[1]

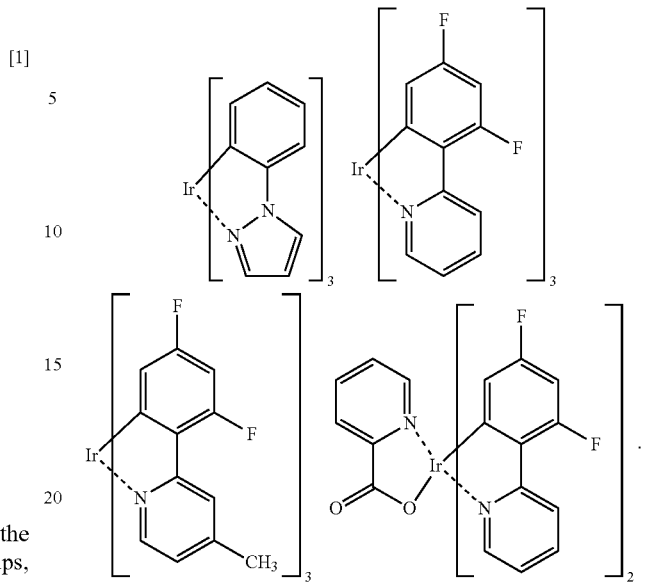

wherein $R_1$ to $R_8$ are independently selected from the group consisting of hydrogen atoms, phenyl groups, biphenyl groups, terphenyl groups, naphthyl groups, phenanthryl groups, triphenylene groups, fluorenyl groups, dibenzothiophene groups, carbonyl groups, amino groups, and spiro[cyclopenta[def]triphenylene-4,9'-fluorene] groups, wherein the phenyl groups, the biphenyl groups, the terphenyl groups, the naphthyl groups, the phenanthryl groups, the triphenylene groups, the fluorenyl groups, the dibenzothiophene groups, the carbonyl groups, the amino groups, and the spiro[cyclopenta[def]triphenylene-4,9'-fluorene] groups optionally have substituents selected from alkyl groups, phenyl groups, carbonyl groups having phenyl groups, substituted amino groups, and dibenzothiophene groups;

wherein R8 is selected from the group consisting of phenyl groups, biphenyl groups, terphenyl groups, naphthyl groups, phenanthryl groups, triphenylene groups, fluorenyl groups, dibenzothiophene groups, carbonyl groups, amino groups, and spiro[cyclopenta[def]triphenylene-4,9'-fluorene] groups.

2. An organic light-emitting device comprising a pair of electrodes and an organic compound layer disposed between the electrodes, wherein the organic compound layer includes a spiro[cyclopenta[def]triphenylene-4,9'-fluorene] compound according to claim 1.

3. The organic light-emitting device according to claim 2, wherein the organic compound layer is a light-emitting layer or an electron-transporting layer.

4. The organic light-emitting device according to claim 3, wherein the organic compound layer is a light-emitting layer.

5. The organic light-emitting device according to claim 4, wherein the light-emitting layer includes a host material and a guest material, and wherein the host material is the spiro[cyclopenta[def]triphenylene-4,9'-fluorene] compound.

6. The organic light-emitting device according to claim 5, wherein the guest material is a phosphorescent material.

7. The organic light-emitting device according to claim 6, wherein the phosphorescent material is an iridium complex.

8. The organic light-emitting device according to claim 7, wherein the iridium complex emits blue light.

9. The organic light-emitting device according to claim 8, wherein the iridium complex is selected from the following compounds 10. A display comprising a plurality of pixels, wherein the pixels each include the organic light-emitting device according to claim 2 and a switching device connected to the organic light-emitting device.

11. An image input apparatus comprising a display section for displaying an image and an input section for inputting image information, wherein the display section includes a plurality of pixels each having the organic light-emitting device according to claim 2 and a switching device connected to the organic light-emitting device.

12. A lighting system comprising the organic light-emitting device according to claim 2 and a switching device connected to the organic light-emitting device.

13. An electrographic image-forming apparatus comprising an exposure light source; the exposure light source comprises the organic light-emitting device according to claim 2.

14. An exposing light source of an electrographic image-forming apparatus comprising the organic light-emitting device according to claim 2.

15. An image pick up apparatus comprising a display portion, the display portion comprising a plurality of pixels, wherein the pixels each include the organic light-emitting device according to claim 2 and a switching device.

16. The spiro[cyclopenta[def]triphenylene-4,9'-fluorene] compound according to claim 1,
wherein at least one of the R5 to R7 is selected from group consisting of the phenyl groups, the biphenyl groups, the terphenyl groups, the naphthyl groups, the phenanthryl groups, the triphenylene groups, the fluorenyl groups, the dibenzothiophene groups, the carbonyl groups, the amino groups, and the spiro[cyclopenta[def]triphenylene-4,9'-fluorene] groups.

17. A device comprising:
a pair of electrodes; and
an organic compound layer disposed between the pair of electrodes;
wherein the organic compound layer comprises the spiro[cyclopenta[def]triphenylene-4,9'-fluorene] compound according to claim 1.

18. An organic light-emitting device comprising a pair of electrodes and a light emitting layer disposed between the electrodes, wherein the light emitting layer includes a host material and a guest material, wherein the host material is essentially consisting of the spiro[cyclopenta[def]triphenylene-4,9'-fluorene] compound represented by the following General Formula [1]:

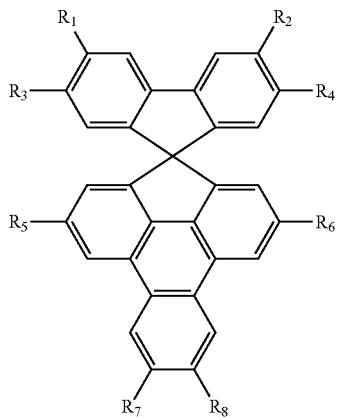

wherein $R_1$ to $R_8$ are independently selected from the group consisting of hydrogen atoms, phenyl groups, biphenyl groups, terphenyl groups, naphthyl groups, phenanthryl groups, triphenylene groups, fluorenyl groups, dibenzothiophene groups, carbonyl groups, amino groups, and spiro[cyclopenta[def]triphenylene-4,9'-fluorene] groups, and wherein the phenyl groups, the biphenyl groups, the terphenyl groups, the naphthyl groups, the phenanthryl groups, the triphenylene groups, the fluorenyl groups, the dibenzothiophene groups, the carbonyl groups, the amino groups, and the spiro[cyclopenta[def]triphenylene-4,9'-fluorene] groups optionally have substituents selected from alkyl groups, phenyl groups, carbonyl groups having phenyl groups, substituted amino groups, and dibenzothiophene groups;

wherein the R8 is selected from a group consisting of the phenyl groups, the biphenyl groups, the terphenyl groups, the naphthyl groups, the phenanthryl groups, the triphenylene groups, the fluorenyl groups, the dibenzothiophene groups, the carbonyl groups, the amino groups, and the spiro[cyclopenta[def]triphenylene-4,9'-fluorene] groups.

19. The organic light-emitting device according to claim 18, wherein at least one of the R5 to R7 is selected from a group consisting of the phenyl groups, the biphenyl groups, the terphenyl groups, the naphthyl groups, the phenanthryl groups, the triphenylene groups, the fluorenyl groups, the dibenzothiophene groups, the carbonyl groups, the amino groups, and the spiro[cyclopenta[def]triphenylene-4,9'-fluorene] groups.

* * * * *